United States Patent
Fukuda et al.

(10) Patent No.: US 11,443,430 B2
(45) Date of Patent: *Sep. 13, 2022

(54) DIAGNOSIS SUPPORT DEVICE, DIAGNOSIS SUPPORT METHOD, AND DIAGNOSIS SUPPORT PROGRAM

(71) Applicant: FUJIFILM Corporation, Tokyo (JP)

(72) Inventors: Takeshi Fukuda, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 177 days.

This patent is subject to a terminal disclaimer.

(21) Appl. No.: 16/915,716

(22) Filed: Jun. 29, 2020

(65) Prior Publication Data

US 2021/0012498 A1 Jan. 14, 2021

(30) Foreign Application Priority Data

Jul. 12, 2019 (JP) ............................. JP2019-130713

(51) Int. Cl.
  G06T 7/00 (2017.01)
  A61B 6/00 (2006.01)
  G06N 20/00 (2019.01)
  G06V 40/10 (2022.01)

(52) U.S. Cl.
  CPC .......... *G06T 7/0014* (2013.01); *A61B 6/5217* (2013.01); *G06N 20/00* (2019.01); *G06V 40/10* (2022.01); *G06T 2207/20081* (2013.01); *G06T 2207/30096* (2013.01)

(58) Field of Classification Search
  CPC ......... G06T 7/0014; G06T 2207/20081; G06T 2207/30096; G06N 20/00; G06V 40/10; A16B 6/5217
  See application file for complete search history.

(56) References Cited

U.S. PATENT DOCUMENTS

| | | | |
|---|---|---|---|
| 11,327,773 B2* | 5/2022 | Hermosillo Valadez | .................... G06F 3/0482 |
| 2006/0250131 A1* | 11/2006 | Reeder | ............... G01R 33/4828 324/309 |
| 2011/0144482 A1* | 6/2011 | Sendai | .................. G06T 7/0012 600/425 |
| 2019/0057504 A1* | 2/2019 | Kobayashi | ........... G06K 9/6271 |

FOREIGN PATENT DOCUMENTS

| | | |
|---|---|---|
| JP | 2019-33966 A | 3/2019 |
| KR | 101880678 B1 * | 7/2018 |

* cited by examiner

*Primary Examiner* — Khai M Nguyen
(74) *Attorney, Agent, or Firm* — Birch, Stewart, Kolasch & Birch, LLP

(57) ABSTRACT

A diagnosis support device acquires medical image data representing a medical image obtained by imaging an animal as a subject with a medical image capturing device and head species information representing a head species of the subject and determines presence or absence of an abnormality in the medical image of the subject based on the acquired medical image data and head species information and a learned model learned in advance using a set of a plurality of pieces of the medical image data for learning and the head species information.

10 Claims, 20 Drawing Sheets

FIG. 3
Lateral
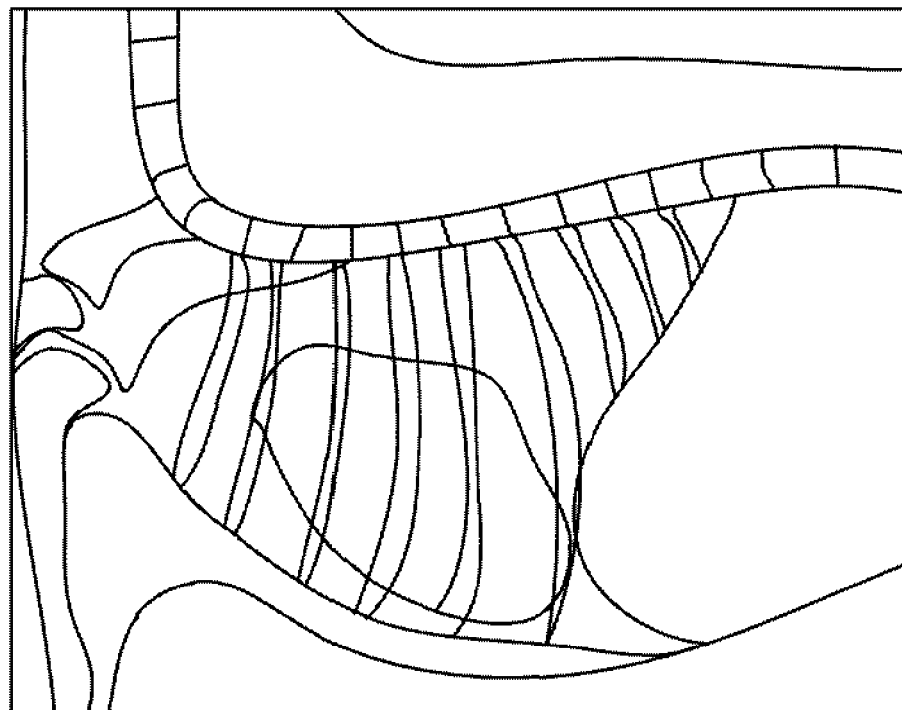
Ventral-Dorsal
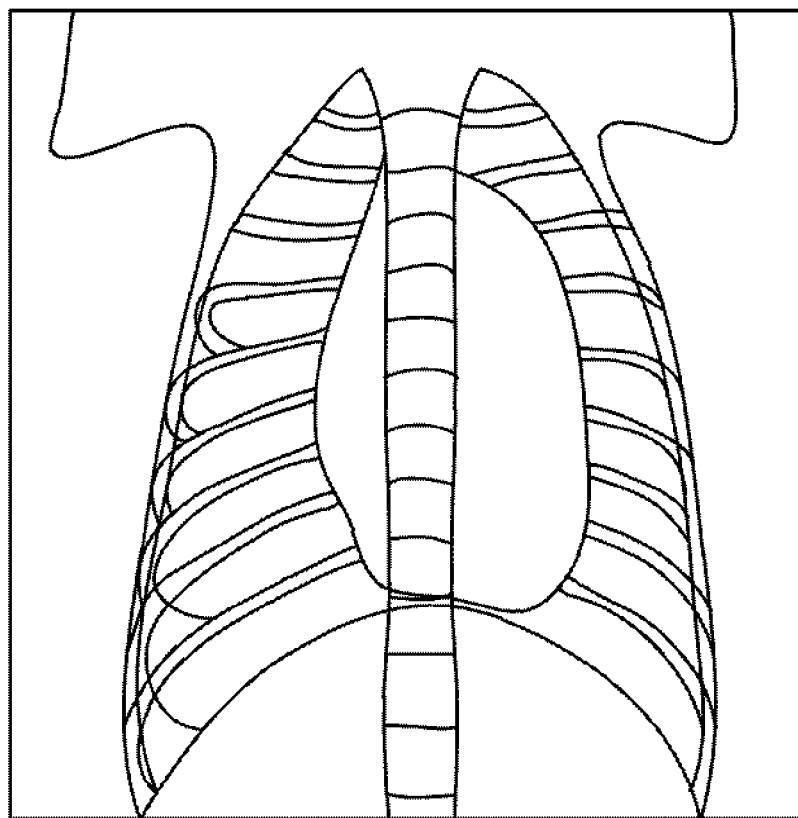

FIG. 4

SHORT-HEADED SPECIES

MIDDLE-HEADED SPECIES

LONG-HEADED SPECIES
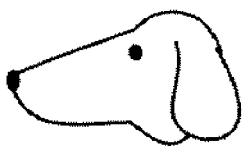

34

MEDICAL IMAGE (SHORT-HEADED SPECIES: NORMAL)

MEDICAL IMAGE (SHORT-HEADED SPECIES: ABNORMAL)

MEDICAL IMAGE (MIDDLE-HEADED SPECIES: NORMAL)

MEDICAL IMAGE (MIDDLE-HEADED SPECIES: ABNORMAL)

MEDICAL IMAGE (LONG-HEADED SPECIES: NORMAL)

MEDICAL IMAGE (LONG-HEADED SPECIES: ABNORMAL)

FIG. 5

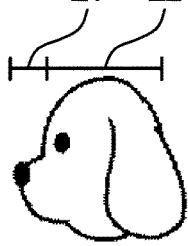

SHORT-HEADED SPECIES

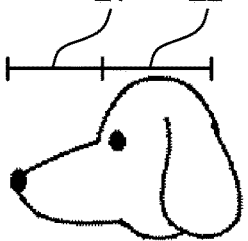

MIDDLE-HEADED SPECIES

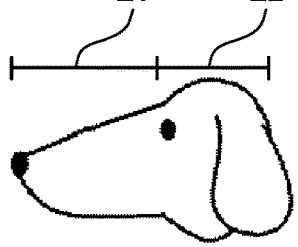

LONG-HEADED SPECIES

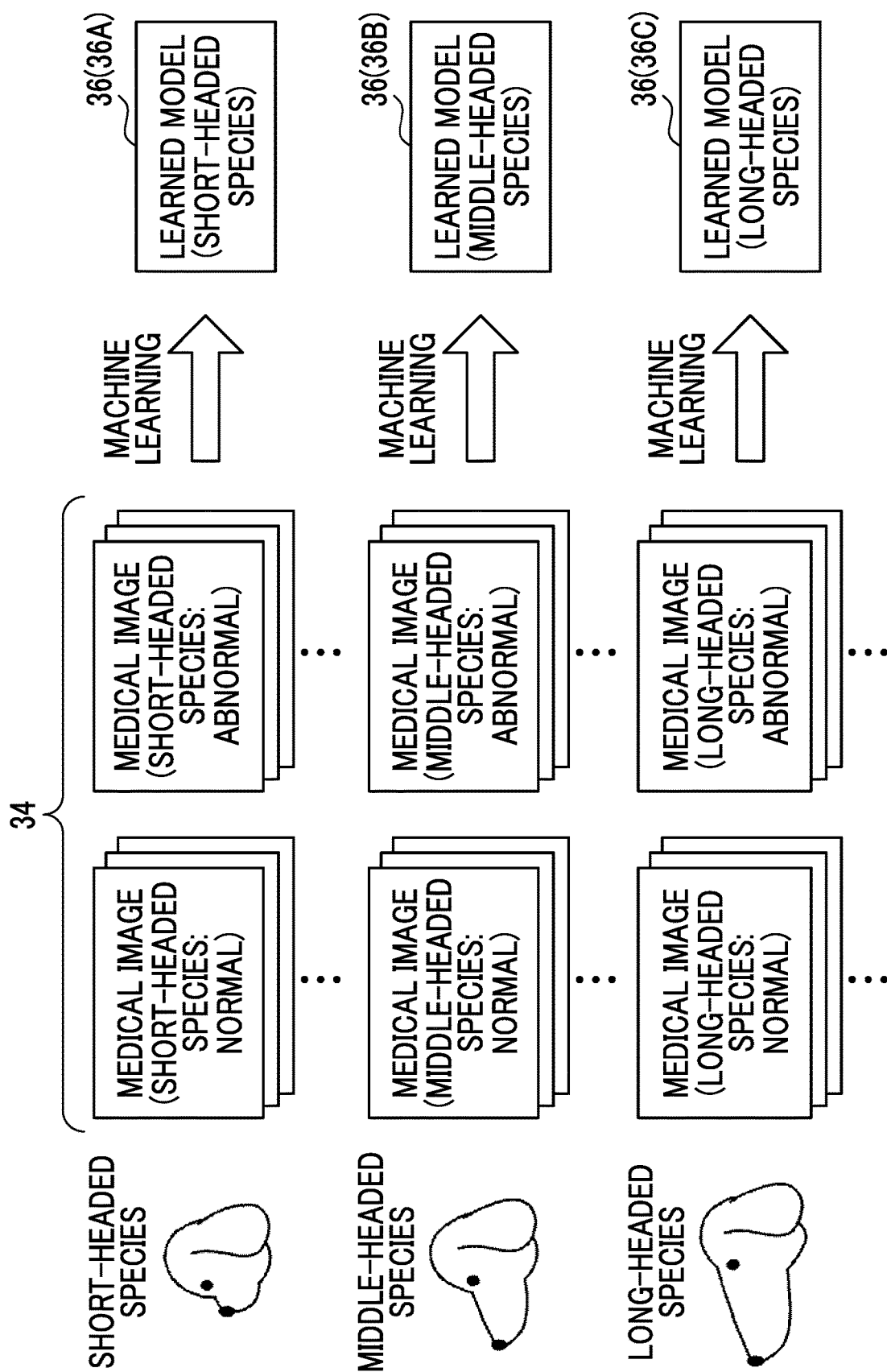

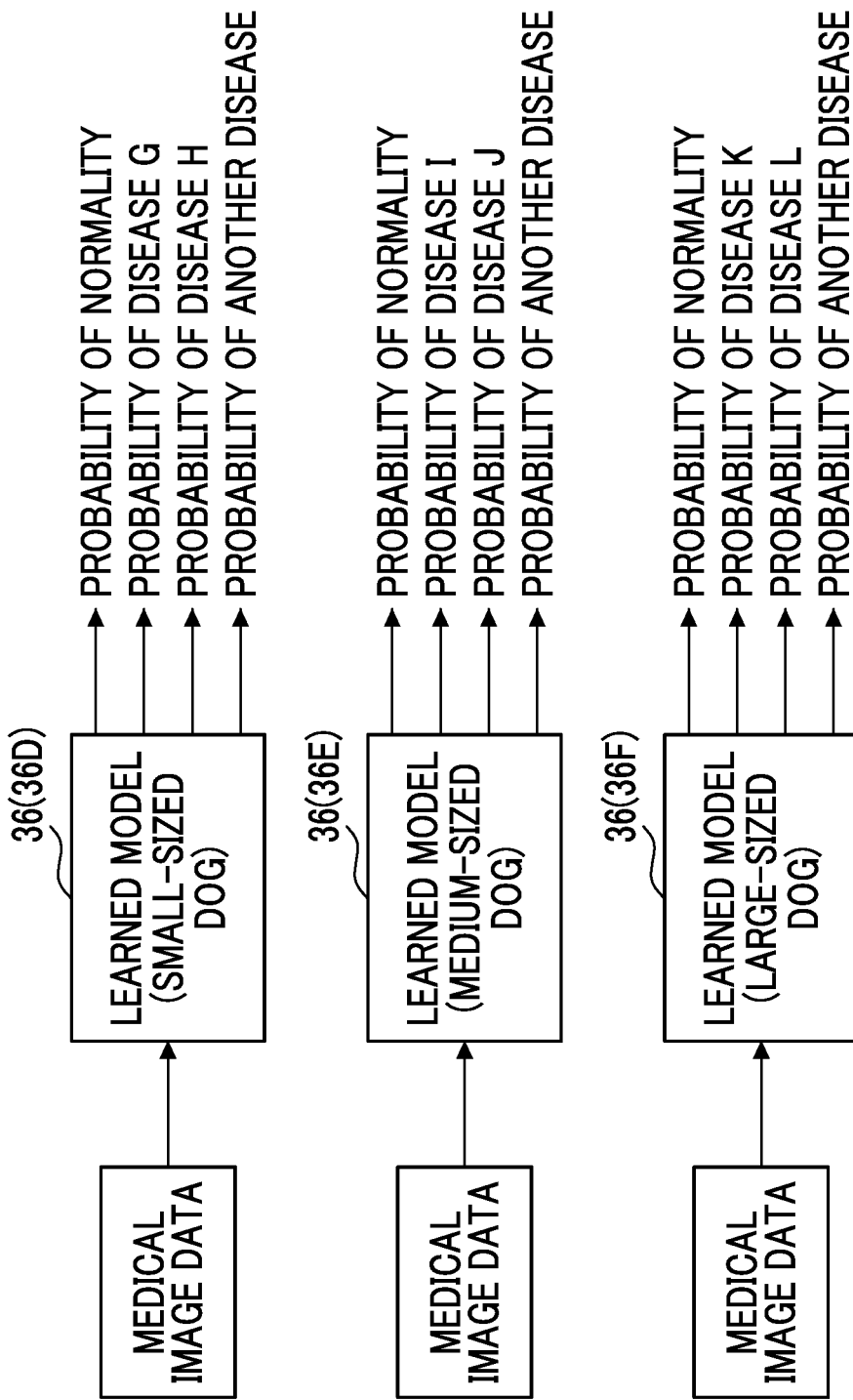

DIAGNOSIS SUPPORT DEVICE, DIAGNOSIS SUPPORT METHOD, AND DIAGNOSIS SUPPORT PROGRAM

CROSS-REFERENCE TO RELATED APPLICATIONS

The present application claims priority under 35 U.S.C. § 119 to Japanese Patent Application No., 2019-130713 filed on Jul. 12, 2019. The above application is hereby expressly incorporated by reference, in its entirety, into the present application.

BACKGROUND

1. Technical Field

The present disclosure relates to a diagnosis support device, a diagnosis support method, and a diagnosis support program.

2. Description of the Related Art

There is disclosed a technique of performing image analysis on a medical image obtained by capturing a person with a medical image capturing device, using a learned identifier (refer to JP2019-033966A). In this technique, a lesion pattern to which the medical image corresponds among a plurality of types of lesion patterns is determined by the image analysis using the learned identifier.

SUMMARY

By the way, in a case where a subject is an animal, shapes, sizes, positions, and the like of an organ and a bone may be different for each head species. In this case, the presence or absence of a lesion may not be accurately determined by the technique of determining the presence or absence of the lesion only from the medical image without considering the head species as described in JP2019-033966A. In this case, it is impossible to effectively support a diagnosis using the medical image by a user such as a veterinarian.

The present disclosure has been made in view of the above circumstances and provides a diagnosis support device, a diagnosis support method, and a diagnosis support program capable of effectively supporting a diagnosis using a medical image.

In order to achieve the above object, a diagnosis support device according to the present disclosure comprises an acquisition unit that acquires medical image data representing a medical image obtained by imaging an animal as a subject with a medical image capturing device and head species information representing a head species of the subject, and a determination unit that determines presence or absence of an abnormality in the medical image of the subject based on the medical image data and the head species information acquired by the acquisition unit and a learned model learned in advance using a set of a plurality of pieces of the medical image data for learning and the head species information.

In the diagnosis support device according to the present disclosure, the plurality of pieces of the medical image data for learning may include first medical image data representing a first medical image not including a lesion and second medical image data representing a second medical image including a lesion corresponding to a disease.

In the diagnosis support device according to the present disclosure, the second medical image may include a medical image classified for each disease determined in advance as a disease that is likely to be suffered for each head species.

In the diagnosis support device according to the present disclosure, the determination unit may determine the head species of the subject, using an optical image obtained by imaging a head portion of the subject, and the acquisition unit may acquire the head species information representing the head species of the subject determined by the determination unit.

In the diagnosis support device according to the present disclosure, the subject may be a dog, and the head species may be a short-headed species, a middle-headed species, or a long-headed species.

A diagnosis support method according to the present disclosure executed by a computer includes acquiring medical image data representing a medical image obtained by imaging an animal as a subject with a medical image capturing device and head species information representing a head species of the subject, and determining presence or absence of an abnormality in the medical image of the subject based on the acquired medical image data and head species information and a learned model learned in advance using a set of a plurality of pieces of the medical image data for learning and the head species information.

A diagnosis support program according to the present disclosure causes a computer to execute processing of acquiring medical image data representing a medical image obtained by imaging an animal as a subject with a medical image capturing device and head species information representing a head species of the subject, and determining presence or absence of an abnormality in the medical image of the subject based on the acquired medical image data and head species information and a learned model learned in advance using a set of a plurality of pieces of the medical image data for learning and the head species information.

The diagnosis support device according to the present disclosure comprises a memory that stores a command to be executed by a computer and a processor configured to execute the stored command. The processor acquires medical image data representing a medical image obtained by imaging an animal as a subject with a medical image capturing device and head species information representing a head species of the subject, and determines presence or absence of an abnormality in the medical image of the subject based on the acquired medical image data and head species information and a learned model learned in advance using a set of a plurality of pieces of the medical image data for learning and the head species information.

According to the present disclosure, it is possible to effectively support a diagnosis using a medical image.

BRIEF DESCRIPTION OF THE DRAWINGS

FIG. 3 is a diagram showing an example of a medical image.

FIG. 4 is a diagram for describing information added to medical image data according to a first embodiment.

FIG. 5 is a diagram for describing head species.

FIG. 6 is a diagram for describing a learned model for each head species according to the first embodiment.

FIG. 30 is a diagram for describing outputs of the learned models according to the modification example.

DETAILED DESCRIPTION

Hereinafter, examples of the technique of the present disclosure will be described in detail with reference to drawings. In each of the following embodiments, an example in which a dog is employed as an animal as a subject will be described. The "animal" in the present specification means an animal excluding a "human", such as a dog and a cat.

First Embodiment

Figure 1:
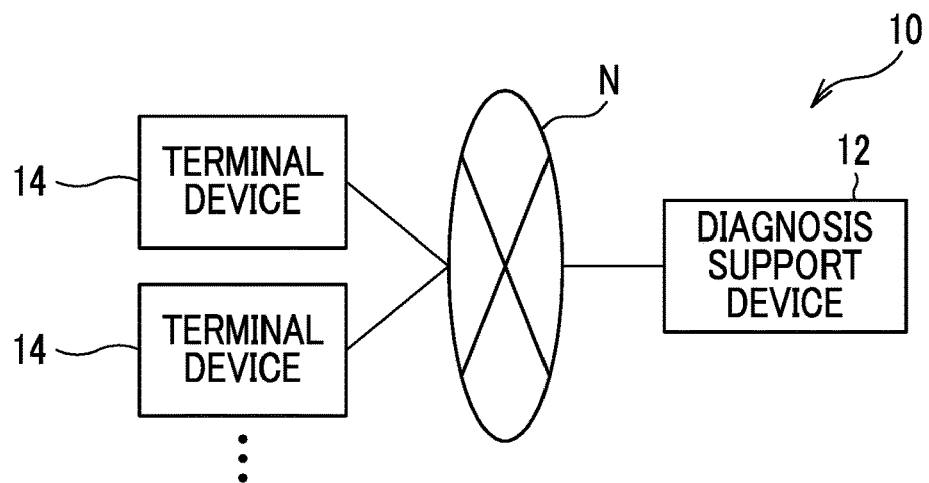
FIG. 1 is a block diagram showing an example of a configuration of an information processing system according to each embodiment.

First, a configuration of an information processing system 10 according to the present embodiment will be described with reference to FIG. 1. As shown in FIG. 1, the information processing system 10 includes a diagnosis support device 12 and a plurality of terminal devices 14. The diagnosis support device 12 and the plurality of terminal devices 14 are respectively connected to a network N and can communicate with each other through the network N.

The diagnosis support device 12 is installed in, for example, an animal hospital. An example of the diagnosis support device 12 is a server computer or the like. The diagnosis support device 12 may be a cloud server. The terminal device 14 is installed in, for example, the animal hospital and is used by a user such as a veterinarian. Examples of the terminal device 14 include a personal computer and a tablet computer.

Figure 2:
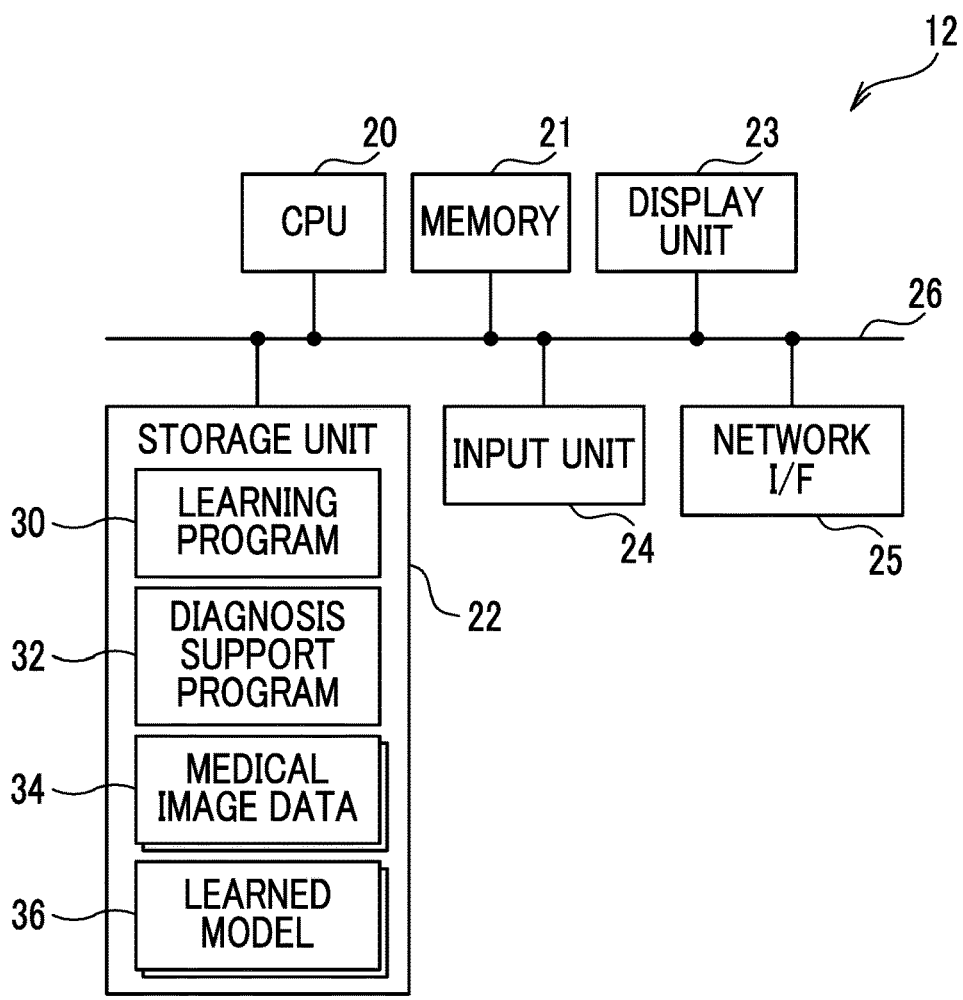
FIG. 2 is a block diagram showing an example of a hardware configuration of a diagnosis support device according to each embodiment.

Next, a hardware configuration of the diagnosis support device 12 according to the present embodiment will be described with reference to FIG. 2. As shown in FIG. 2, the diagnosis support device 12 includes a central processing unit (CPU) 20, a memory 21 as a temporary storage area, and a nonvolatile storage unit 22. The diagnosis support device 12 includes a display unit 23 such as a liquid crystal display, an input unit 24 such as a keyboard and a mouse, and a network interface (I/F) 25 connected to the network N. The CPU 20, the memory 21, the storage unit 22, the display unit 23, the input unit 24, and the network I/F 25 are connected to a bus 26.

The storage unit 22 is formed of a hard disk drive (HDD), a solid state drive (SSD), a flash memory, or the like. The storage unit 22 as a storage medium stores a learning program 30. The CPU 20 reads out the learning program 30 from the storage unit 22, then develops the program in the memory 21, and executes the developed learning program 30. The storage unit 22 stores a diagnosis support program 32. The CPU 20 reads out the diagnosis support program 32 from the storage unit 22, then develops the program in the memory 21, and executes the developed diagnosis support program 32. The storage unit 22 stores a plurality of pieces of medical image data 34 for learning and a learned model 36.

The medical image data 34 is image data representing a medical image obtained by imaging the dog as the subject with a medical image capturing device. In the present embodiment, an example will be described in which image data representing a radiographic image according to a radiation amount detected by a radiation detector that irradiates radiation to the dog as the subject and detects radiation transmitted through the dog is employed as the medical image data 34. The medical image data 34 may be image data representing a magnetic resonance imaging (MRI) image, image data representing a computed tomography (CT) image, or the like.

As shown in FIG. 3 as an example, the medical image data 34 is a set of medical image data representing a medical image obtained by imaging an imaging target portion of the dog in a side surface direction (so-called Lateral) and medical image data representing a medical image obtained by imaging the imaging target portion thereof in a direction from an abdominal side toward a back side (so-called "Ventral-Dorsal"). The medical image data 34 may be medical image data representing a medical image obtained by imaging the imaging target portion thereof from one direction or may be a set of medical image data representing medical images obtained by imaging the imaging target portion thereof from three or more directions.

As shown in FIG. 4 as an example, head species information indicating a head species of the dog to be imaged and information (hereinafter referred to as "abnormality presence/absence information") indicating the presence or absence of an abnormality in the medical image represented by the medical image data 34 are added to the medical image data 34. In the example of FIG. 4, the absence of abnormality is denoted as "normal". Here, a medical image having no abnormality means a medical image including no lesion, and a medical image having an abnormality means a medical image including a lesion corresponding to a disease. In the following, among the plurality of pieces of medical image data 34 for learning, the medical image including no lesion is referred to as a "first medical image" and medical image data representing the first medical image is referred to as "first medical image data". In the following, among the plurality of pieces of medical image data 34 for learning, the medical image including the lesion corresponding to the disease is referred to as a "second medical image" and medical image data representing the second medical image is referred to as "second medical image data".

As shown in FIG. 4, in the present embodiment, an example will be described in which the head species of the dog is a short-headed species, a middle-headed species, or a long-headed species. However, the present disclosure is not limited thereto. The head species of the dog may be two types, for example, short-headed species or long-headed species, or four or more types. As shown in FIG. 5, the short-headed species according to the present embodiment means a dog with a nose length L1 shorter than a skull length L2. The long-headed species means a dog with the nose length L1 longer than the skull length L2. The middle-headed species means a dog with the same nose length L1 and skull length L2. The middle-headed species may include a case where a difference between the nose length L1 and the skull length L2 is within a range of an allowable error even though the nose length L1 and the skull length L2 are not completely the same.

The learned model 36 is a model learned in advance using a set of the plurality of pieces of medical image data 34 for learning and the head species information. In the present embodiment, as shown in FIG. 6 as an example, the learned model 36 is generated for each head species by machine learning using the set of the plurality of pieces of medical image data 34 and the head species information. In the following, in a case where the learned model 36 is distinguished for each head species, the description will be made with an alphabet added to the end of the reference numeral, such as a learned model 36A for the short-headed species, a learned model 36B for the middle-headed species, and a learned model 36C for the long-headed species. An example of the learned model 36 is a neural network model.

Figure 7:
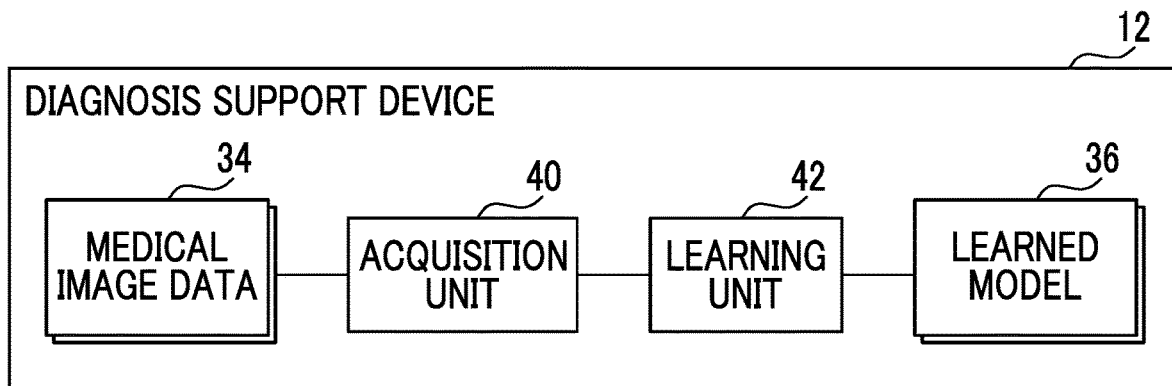
FIG. 7 is a block diagram showing an example of a functional configuration in a learning phase of the diagnosis support device according to the first embodiment.

Next, a functional configuration in a learning phase of the diagnosis support device 12 according to the present embodiment will be described with reference to FIG. 7. As shown in FIG. 7, the diagnosis support device 12 includes an acquisition unit 40 and a learning unit 42. The CPU 20 executes the learning program 30 to function as the acquisition unit 40 and the learning unit 42.

The acquisition unit 40 acquires the medical image data 34, and the head species information and the abnormality presence/absence information added to the medical image data 34, from the storage unit 22.

The learning unit 42 learns a plurality of sets of the medical image data 34, the head species information, and the abnormality presence/absence information acquired by the acquisition unit 40 as learning data (also referred to as teacher data) to generate the learned model 36 that outputs information on the presence or absence of the abnormality in the medical image of the subject based on the medical image data and the head species information.

Specifically, the learning unit 42 generates the learned model 36, by machine learning, that receives the medical image data 34 and outputs the information representing the presence or absence of the abnormality in the medical image represented by the medical image data 34, for each head species represented by the head species information.

More specifically, in a case where the medical image data 34 representing a medical image having no abnormality among the medical image data 34 of the short-headed species is input, the learning unit 42 causes the model to learn such that information representing normality (for example, "0") is output. In a case where the medical image data 34 representing a medical image having the abnormality among the medical image data 34 of the short-headed species is input, the learning unit 42 causes the model to learn such that information representing abnormality (for example, "1") is output. The learned model 36A for the short-headed species is generated by the learning.

Similarly, in a case where the medical image data 34 representing a medical image having no abnormality among the medical image data 34 of the middle-headed species is input, the learning unit 42 causes the model to learn such that information representing normality is output. In a case where the medical image data 34 representing a medical image having the abnormality among the medical image data 34 of the middle-headed species is input, the learning unit 42 causes the model to learn such that information representing abnormality is output. The learned model 36B for the middle-headed species is generated by the learning.

Similarly, in a case where the medical image data 34 representing a medical image having no abnormality among the medical image data 34 of the long-headed species is input, the learning unit 42 causes the model to learn such that information representing normality is output. In a case where the medical image data 34 representing a medical image having the abnormality among the medical image data 34 of the long-headed species is input, the learning unit 42 causes the model to learn such that information representing abnormality is output. The learned model 36C for the long-headed species is generated by the learning.

Figure 8:
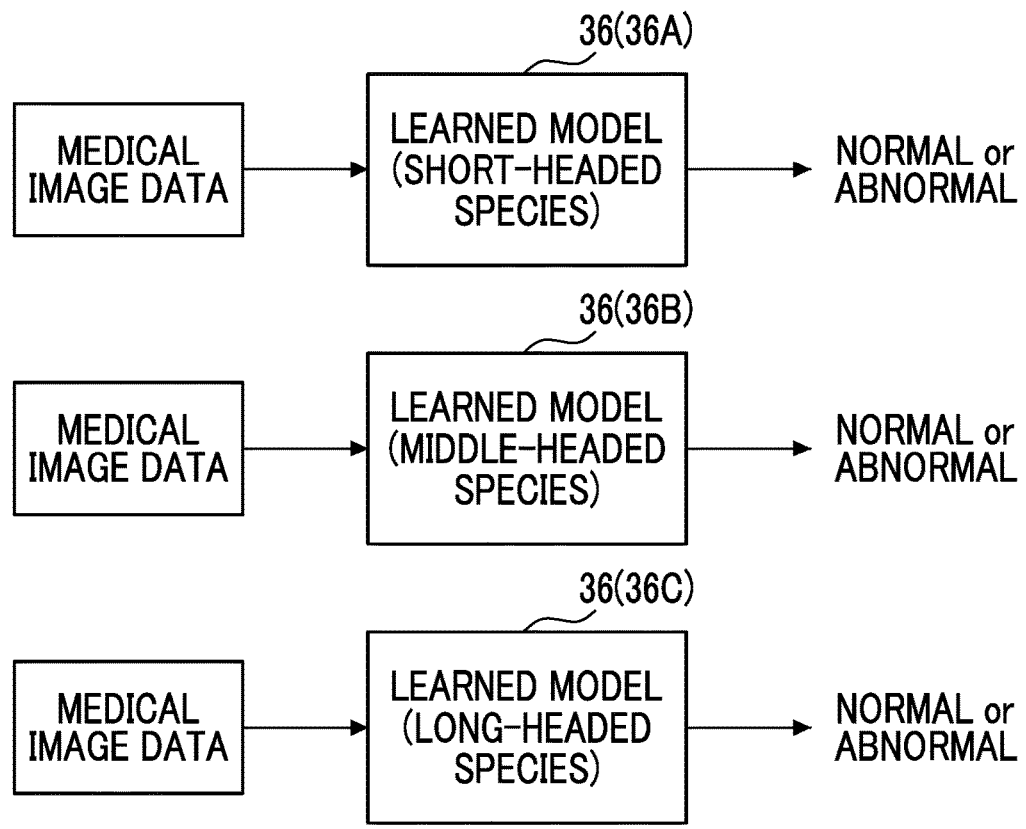
FIG. 8 is a diagram for describing inputs and outputs of the learned models according to the first embodiment.

For example, an error back propagation method can be employed as an algorithm of the learning by the learning unit 42. With the learning by the learning unit 42, as shown in FIG. 8 as an example, the learned model 36 that receives the medical image data and outputs the information representing whether the medical image represented by the received medical image data is normal or abnormal is generated for each head species. The learning unit 42 stores the generated learned model 36 in the storage unit 22.

Next, an action in the learning phase of the diagnosis support device 12 according to the present embodiment will be described with reference to FIG. 9. The CPU 20 executes the learning program 30 to execute learning processing shown in FIG. 9.

Figure 9:
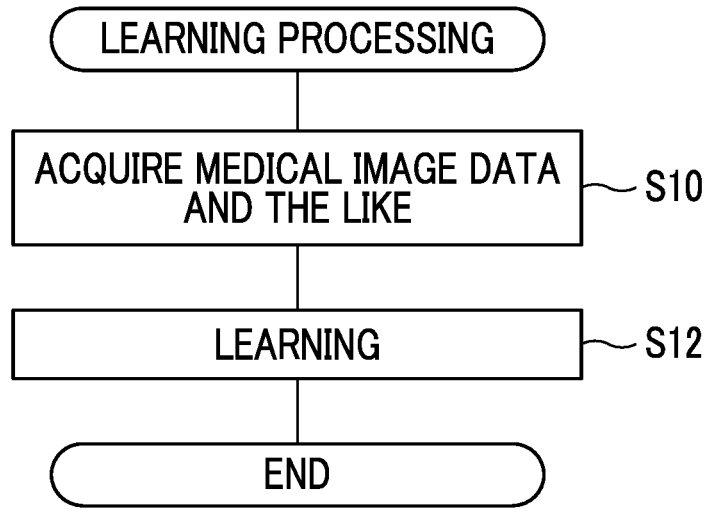
FIG. 9 is a flowchart showing an example of learning processing according to the first embodiment.

In step S10 in FIG. 9, the acquisition unit 40 acquires the medical image data 34, and the head species information and the abnormality presence/absence information added to the medical image data 34, from the storage unit 22.

In step S12, the learning unit 42 causes the model to learn the plurality of sets of the medical image data 34, the head species information, and the abnormality presence/absence information acquired in step S10 as learning data for each head species, as described above. With the learning, the learning unit 42 generates the learned model 36 that outputs the information on the presence or absence of the abnormality in the medical image of the subject based on the medical image data and the head species information. The learning unit 42 stores the generated learned model 36 in the storage unit 22. In a case where the processing of step S12 ends, the learning processing ends.

Figure 10:
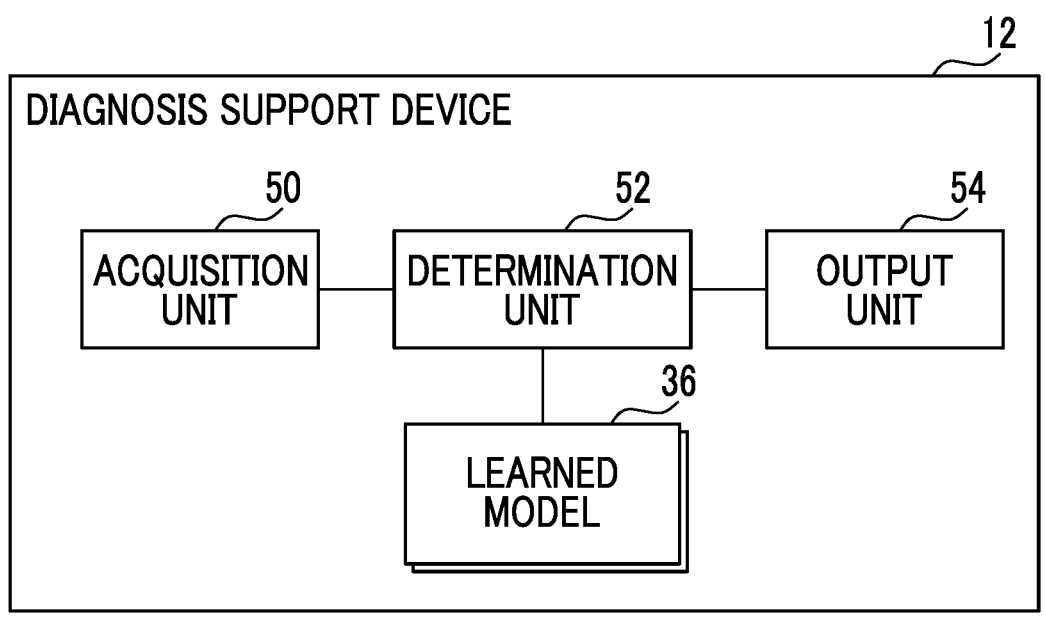
FIG. 10 is a block diagram showing an example of a functional configuration in an operation phase of the diagnosis support device according to the first embodiment.

Next, a functional configuration in an operation phase of the diagnosis support device 12 according to the present embodiment will be described with reference to FIG. 10. As shown in FIG. 10, the diagnosis support device 12 includes an acquisition unit 50, a determination unit 52, and an output unit 54. The CPU 20 executes the diagnosis support program 32 to function as the acquisition unit 50, the determination unit 52, and the output unit 54. The acquisition unit 50 is an example of an acquisition unit according to the disclosed technique, and the determination unit 52 is an example of a determination unit according to the disclosed technique. The diagnosis support device 12 may be the same device or different devices in the learning phase and the operation phase.

The acquisition unit 50 acquires the medical image data representing the medical image obtained by imaging the animal as the subject to be diagnosed by the user such as the veterinarian with the medical image capturing device and the head species information representing the head species of the subject. The head species information may be added to the medical image data or may be input by the user through an operation unit of the terminal device 14. In a state where a table in which a dog breed and the head species are associated with each other is prepared in advance, the acquisition unit 50 may acquire a breed of the dog as the subject from an electronic medical record or the like and then head species information representing a head species corresponding to the acquired dog breed from the table prepared in advance.

The determination unit 52 determines the presence or absence of the abnormality in the medical image of the subject based on the medical image data and the head species information acquired by the acquisition unit 50 and the learned model 36. Specifically, the determination unit 52 inputs the medical image data acquired by the acquisition unit 50 to the learned model 36 for the head species represented by the head species information acquired by the acquisition unit 50. The learned model 36 outputs the information representing normality or the information representing abnormality in correspondence with the input medical image data.

In a case where the output from the learned model 36 is the information representing normality, the determination unit 52 determines that there is no abnormality in the medical image of the subject represented by the medical image data acquired by the acquisition unit 50. On the other hand, in a case where the output from the learned model 36 is the information representing abnormality, the determination unit 52 determines that there is the abnormality in the medical image of the subject represented by the medical image data acquired by the acquisition unit 50.

The output unit 54 outputs information representing the determination result by the determination unit 52. Specifically, the output unit 54 outputs the information representing the determination result by the determination unit 52 to the terminal device 14 to display the determination result by the determination unit 52 on a display unit of the terminal device 14. The user interprets the medical image with reference to the determination result displayed on the display unit of the terminal device 14 and diagnoses the subject.

Next, an action in the operation phase of the diagnosis support device 12 according to the present embodiment will be described with reference to FIG. 11. The CPU 20 executes the diagnosis support program 32 to execute diagnosis support processing shown in FIG. 11.

Figure 11:
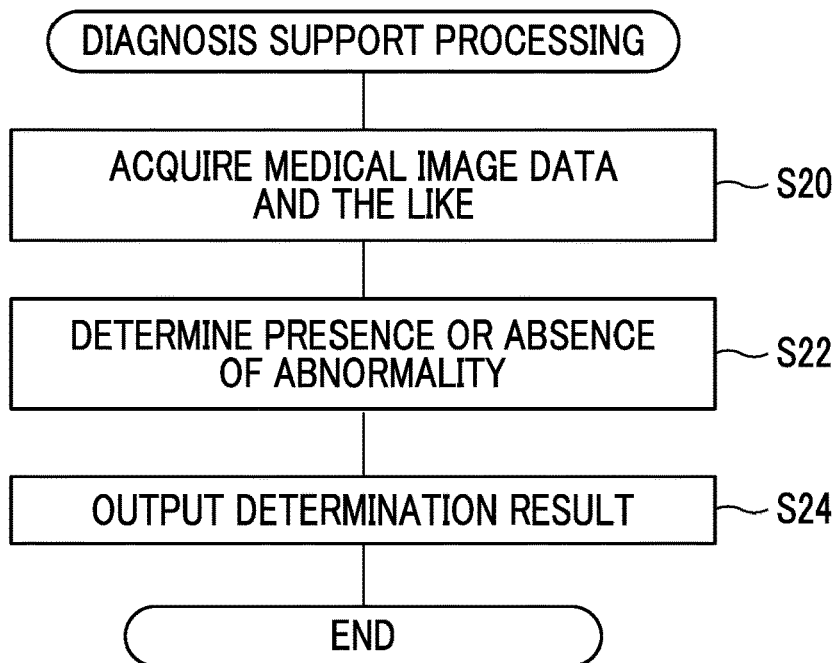
FIG. 11 is a flowchart showing an example of diagnosis support processing according to the first embodiment.

In step S20 in FIG. 11, the acquisition unit 50 acquires the medical image data representing the medical image obtained by imaging the animal as the subject to be diagnosed by the user with the medical image capturing device and the head species information representing the head species of the subject.

In step S22, the determination unit 52 determines the presence or absence of the abnormality in the medical image of the subject based on the medical image data and the head species information acquired in step S20 and the learned model 36, as described above. In step S24, the output unit 54 outputs the information representing the determination result of the processing of step S22 as described above. In a case where the processing of step S24 ends, the diagnosis support processing ends.

Figure 12:
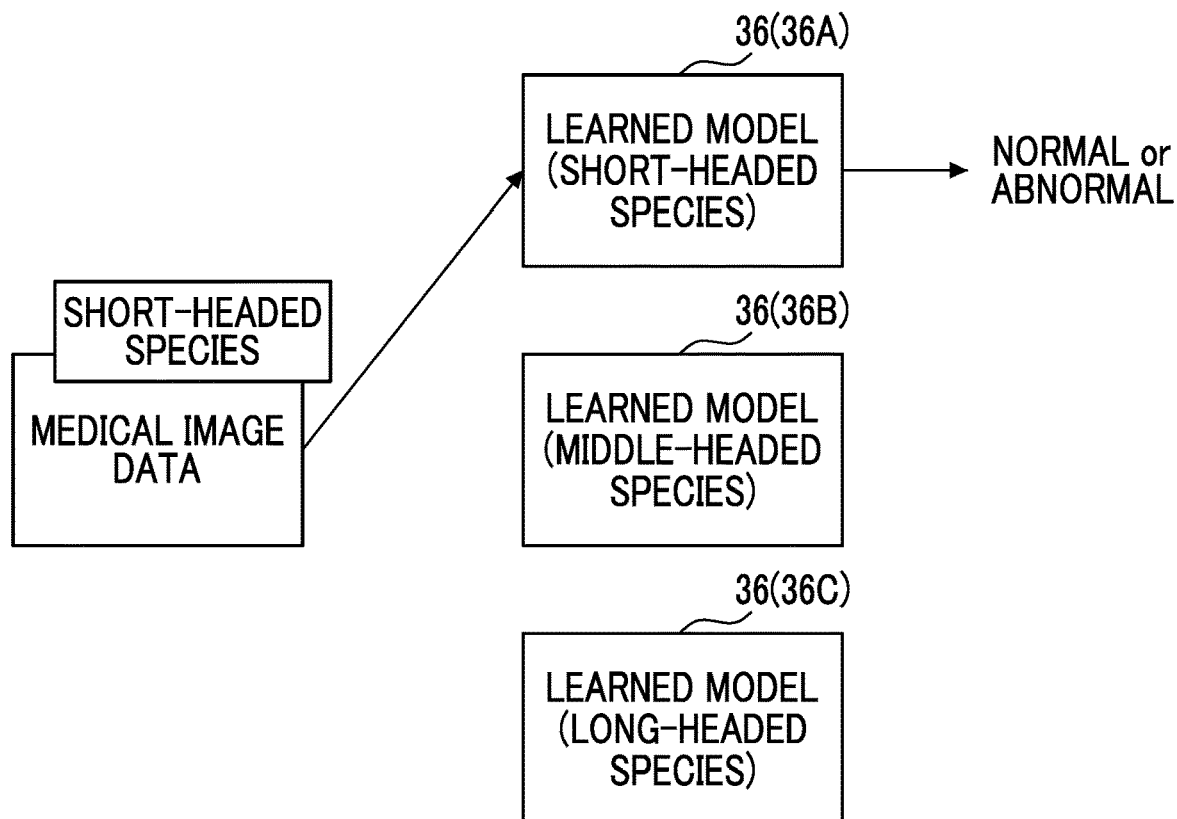
FIG. 12 is a diagram showing determination processing using a learned model for short-headed species.
Figure 13:
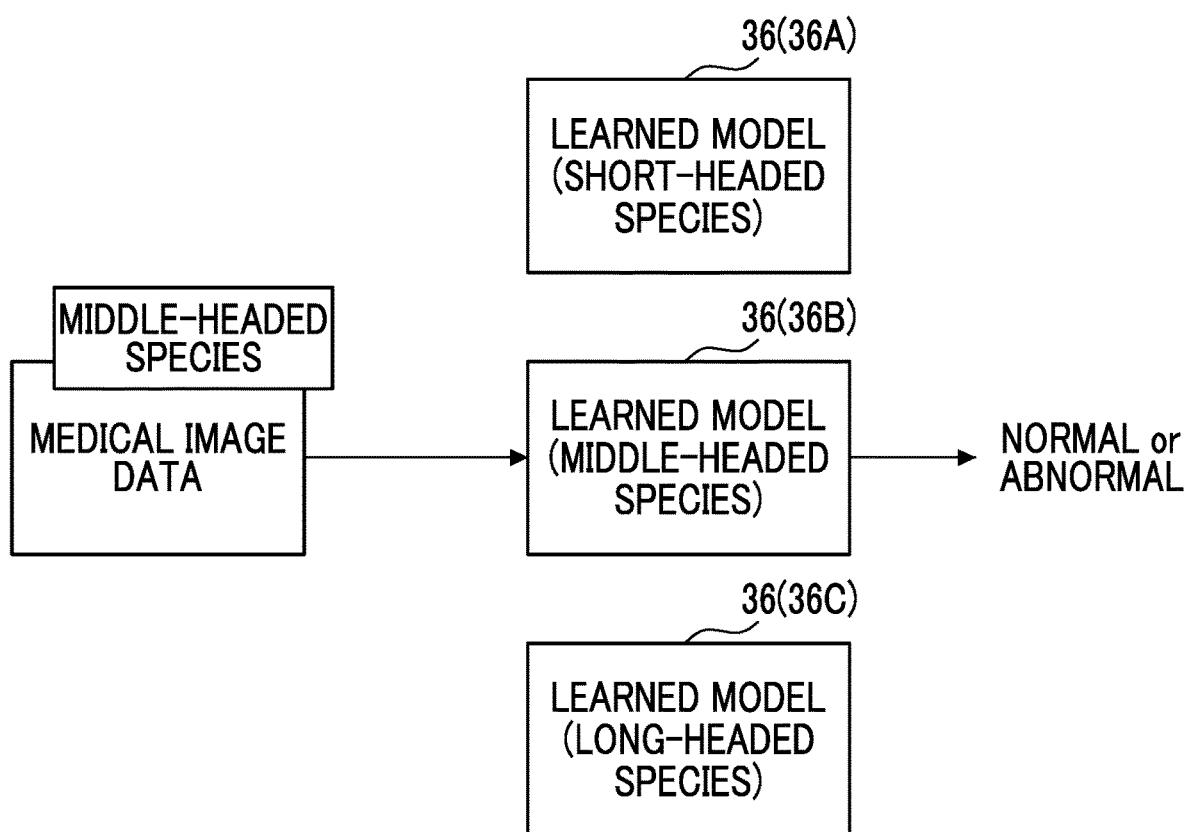
FIG. 13 is a diagram showing determination processing using a learned model for middle-headed species.
Figure 14:
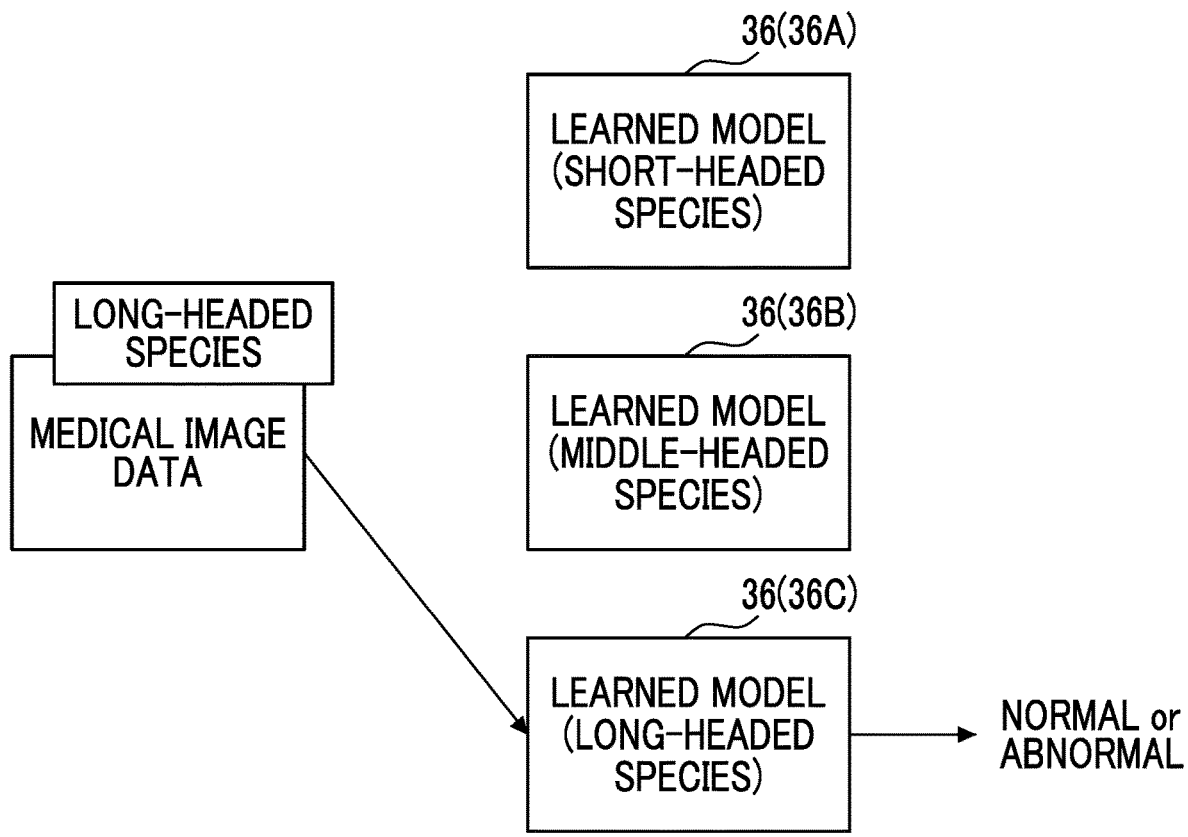
FIG. 14 is a diagram showing determination processing using a learned model for long-headed species.

As described above, according to the present embodiment, the presence or absence of the abnormality in the medical image of the subject is determined based on the medical image data, the head species information, and the learned model 36. Specifically, as shown in FIG. 12, in a case where the subject is the short-headed species, the medical image data is input to the learned model 36A for the short-headed species and the presence or absence of the abnormality in the medical image is determined. As shown in FIG. 13, in a case where the subject is the middle-headed species, the medical image data is input to the learned model 36B for the middle-headed species and the presence or absence of the abnormality in the medical image is determined. As shown in FIG. 14, in a case where the subject is the long-headed species, the medical image data is input to the learned model 36C for the long-headed species, and the presence or absence of the abnormality in the medical image is determined.

Therefore, it is possible to accurately determine the presence or absence of the abnormality in the medical image in consideration of a difference in feature of the medical image depending on the head species. As a result, it is possible to effectively support the diagnosis using the medical image.

Figure 15:
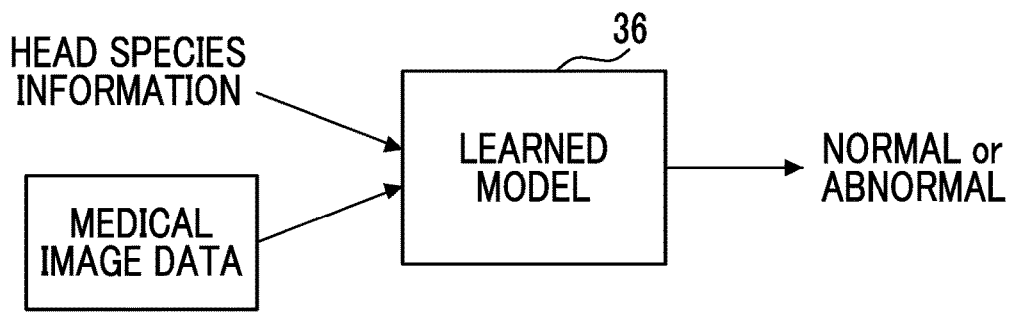
FIG. 15 is a diagram showing an example of a learned model in a case where the medical image data and head species information are input.

In the first embodiment, the case is described in which the learned model 36 that receives the medical image data is generated for each head species. However, the present disclosure is not limited thereto. For example, one learned model 36 that receives the medical image data and the head species information may be generated as shown in FIG. 15.

Figure 16:
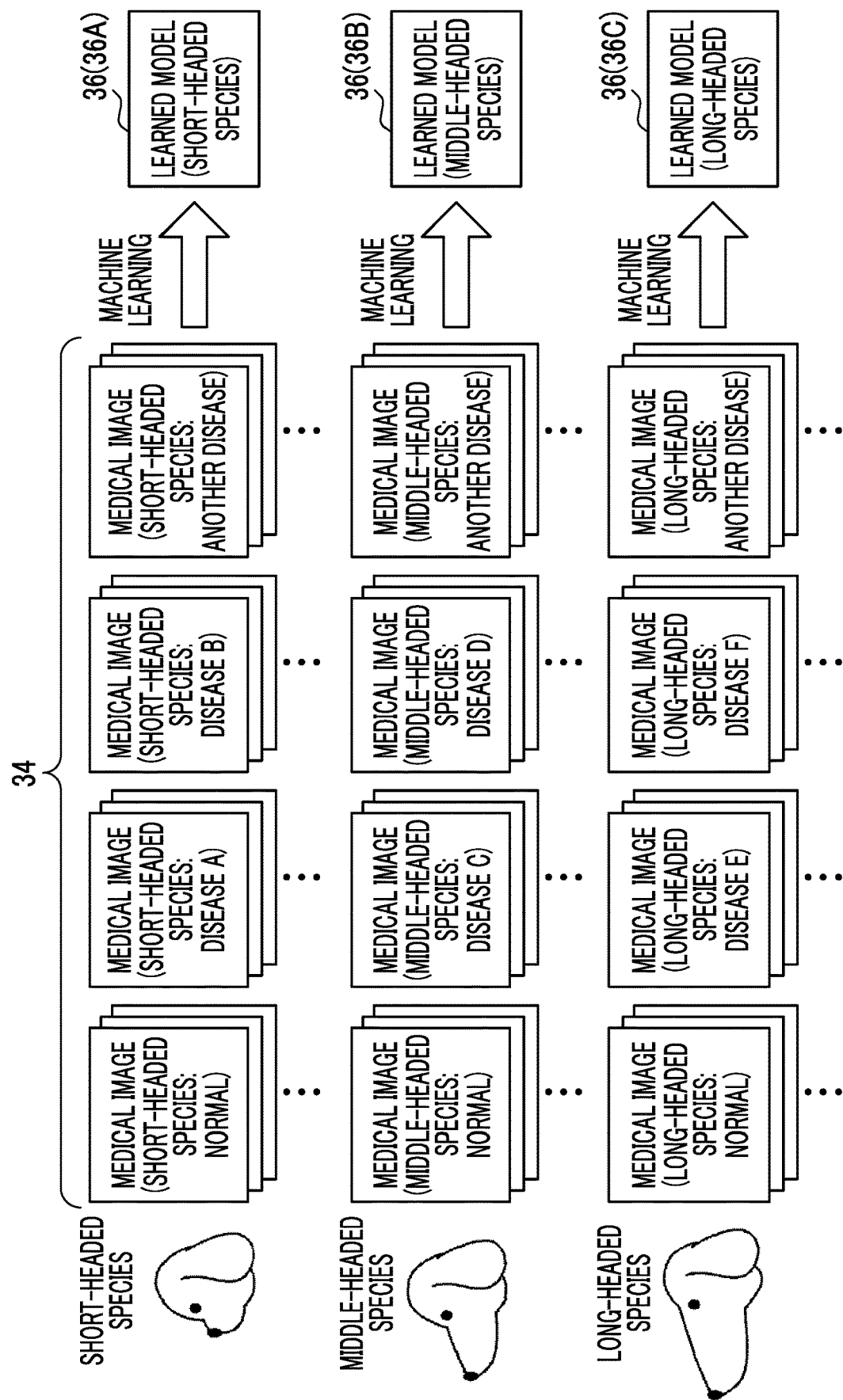
FIG. 16 is a diagram for describing a learned model for each head species according to a modification example.

In the first embodiment, the case is described in which the second medical image including the lesion corresponding to the disease is used as one type of medical image without being classified. However, the present disclosure is not limited thereto. For example, as shown in FIG. 16, the second medical image may be classified for each disease determined in advance as a disease that is likely to be suffered for each head species. FIG. 16 shows an example in which the second medical image of the short-headed species is classified into three types of "disease A", "disease B", and "another disease (that is, disease other than disease A and disease B)". In the example of FIG. 16, the "disease A" and the "disease B" are diseases determined in advance as diseases that the short-headed species is likely to suffer.

Examples of the disease that the short-headed species is likely to suffer include brachycephalic airway syndrome and elongated soft palate.

FIG. 16 shows an example in which the second medical image of the middle-headed species is classified into three types of "disease C", "disease D", and "another disease (that is, disease other than disease C and disease D)". In the example of FIG. 16, the "disease C" and the "disease D" are diseases determined in advance as diseases that the middle-headed species is likely to suffer. Examples of the disease that the middle-headed species is likely to suffer include elongated soft palate and nasal pyoderma.

FIG. 16 shows an example in which the second medical image of the long-headed species is classified into three types of "disease E", "disease F", and "another disease (that is, disease other than disease E and disease F)". In the example of FIG. 16, the "disease E" and the "disease F" are diseases determined in advance as diseases that the long-headed species is likely to suffer. Examples of the disease that the long-headed species is likely to suffer include nasal pyoderma and neoplasms of the nasal cavity.

Figure 17:
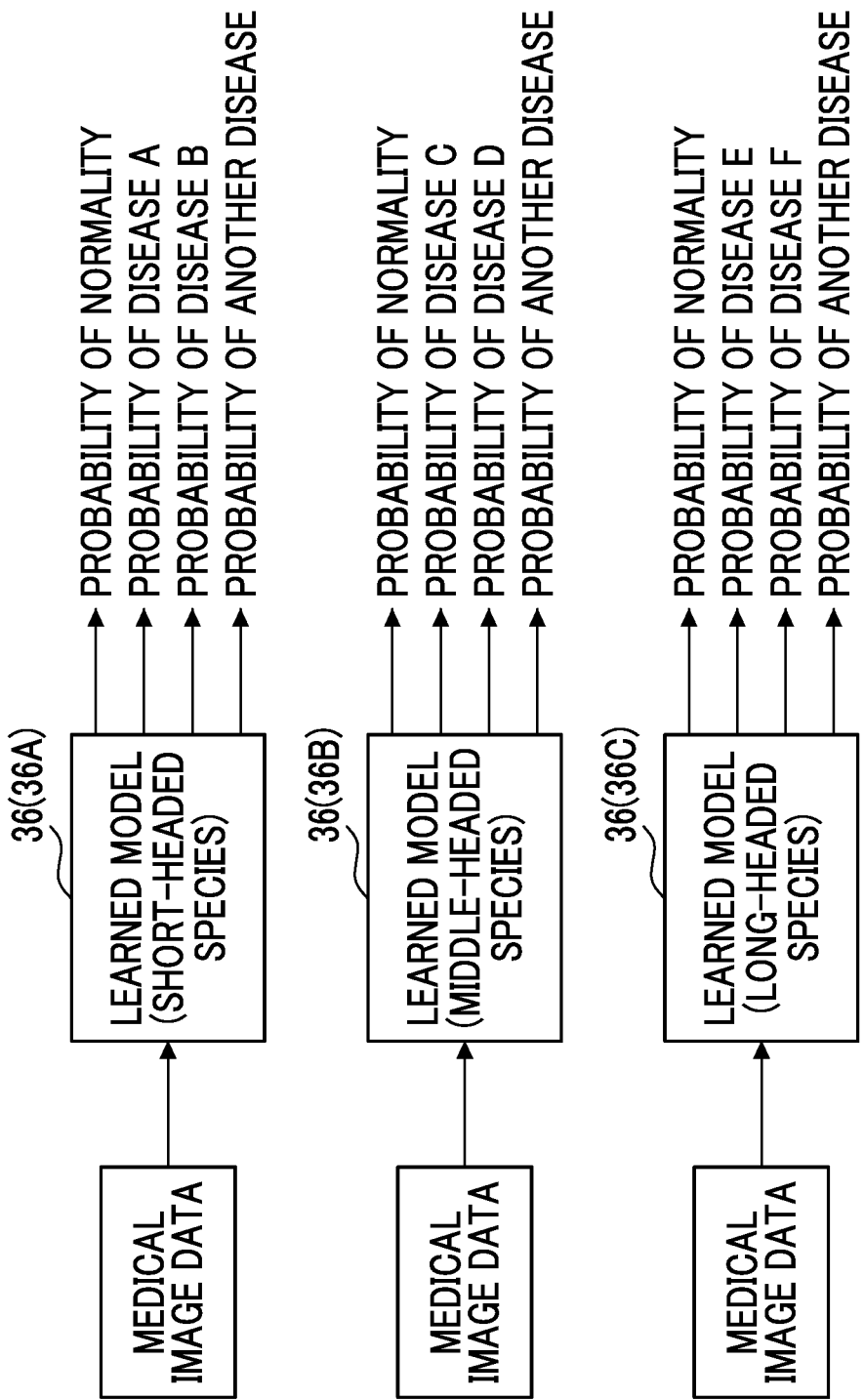
FIG. 17 is a diagram for describing outputs of the learned models according to the modification example.

In this example, as shown in FIG. 17 as an example, a probability that the medical image represented by the input medical image data is normal, a probability that the medical image corresponds to disease A, a probability that the medical image corresponds to disease B, and a probability that the medical image corresponds to another disease are output from the learned model 36A for the short-headed species. In this example, a probability that the medical image represented by the input medical image data is normal, a probability that the medical image corresponds to disease C, a probability that the medical image corresponds to disease D, and a probability that the medical image corresponds to another disease are output from the learned model 36B for the middle-headed species. In this example, a probability that the medical image represented by the input medical image data is normal, a probability that the medical image corresponds to disease E, a probability that the medical image corresponds to disease F, and a probability that the medical image corresponds to another disease are output from the learned model 36C for the long-headed species.

In this example, for example, in a case where the probability that the medical image is normal among the outputs from the learned model 36 is the highest, the determination unit 52 determines that there is no abnormality in the medical image of the subject represented by the medical image data acquired by the acquisition unit 50. In this example, for example, in a case where any probability other than the probability that the medical image is normal among the outputs from the learned model 36 is the highest, the determination unit 52 determines that there is the abnormality in the medical image of the subject represented by the medical image data acquired by the acquisition unit 50. In a case where a total value of the probabilities corresponding to respective diseases other than the probability that the medical image is normal among the outputs from the learned model 36 is higher than the probability that the medical image is normal, the determination unit 52 may determine that there is the abnormality in the medical image of the subject represented by the medical image data acquired by the acquisition unit 50. In this case, in a case where the total value of the probabilities corresponding to respective diseases other than the probability that the medical image is normal among the outputs from the learned model 36 is equal to or less than the probability that the medical image is normal, the determination unit 52 may determine that there is no abnormality in the medical image of the subject represented by the medical image data acquired by the acquisition unit 50. In this example, the medical image data for learning is classified for each easily collected disease. Therefore, it is possible to determine the presence or absence of the disease more accurately.

In this example, in a case where the determination unit 52 determines that there is the abnormality in the medical image of the subject, the output unit 54 may output a disease name to which the medical image corresponds with the highest probability or may output disease names in descending order of the corresponding probability.

In the first embodiment, the determination unit 52 may determine the head species of the subject using an optical image obtained by imaging a head portion of the subject with an imaging device such as a digital camera. In this case, a form is exemplified in which the determination unit 52 performs image analysis processing on the optical image to derive the nose length L1 and the skull length L2 of the subject and compares the derived nose length L1 and skull length L2 of the subject to determine the head species of the subject. In this case, the acquisition unit 50 acquires the head species information representing the head species of the subject determined by the determination unit 52.

Second Embodiment

A second embodiment of the disclosed technique will be described. The configuration of the information processing system 10 according to the present embodiment is the same as that of the first embodiment, and a description thereof will be omitted. The hardware configuration of the diagnosis support device 12 according to the present embodiment is the same as that of the first embodiment except for the plurality of pieces of medical image data 34 for learning and the learned model 36 to be stored in the storage unit 22. Therefore, the medical image data 34 and the learned model 36 will be described herein.

Figure 18:
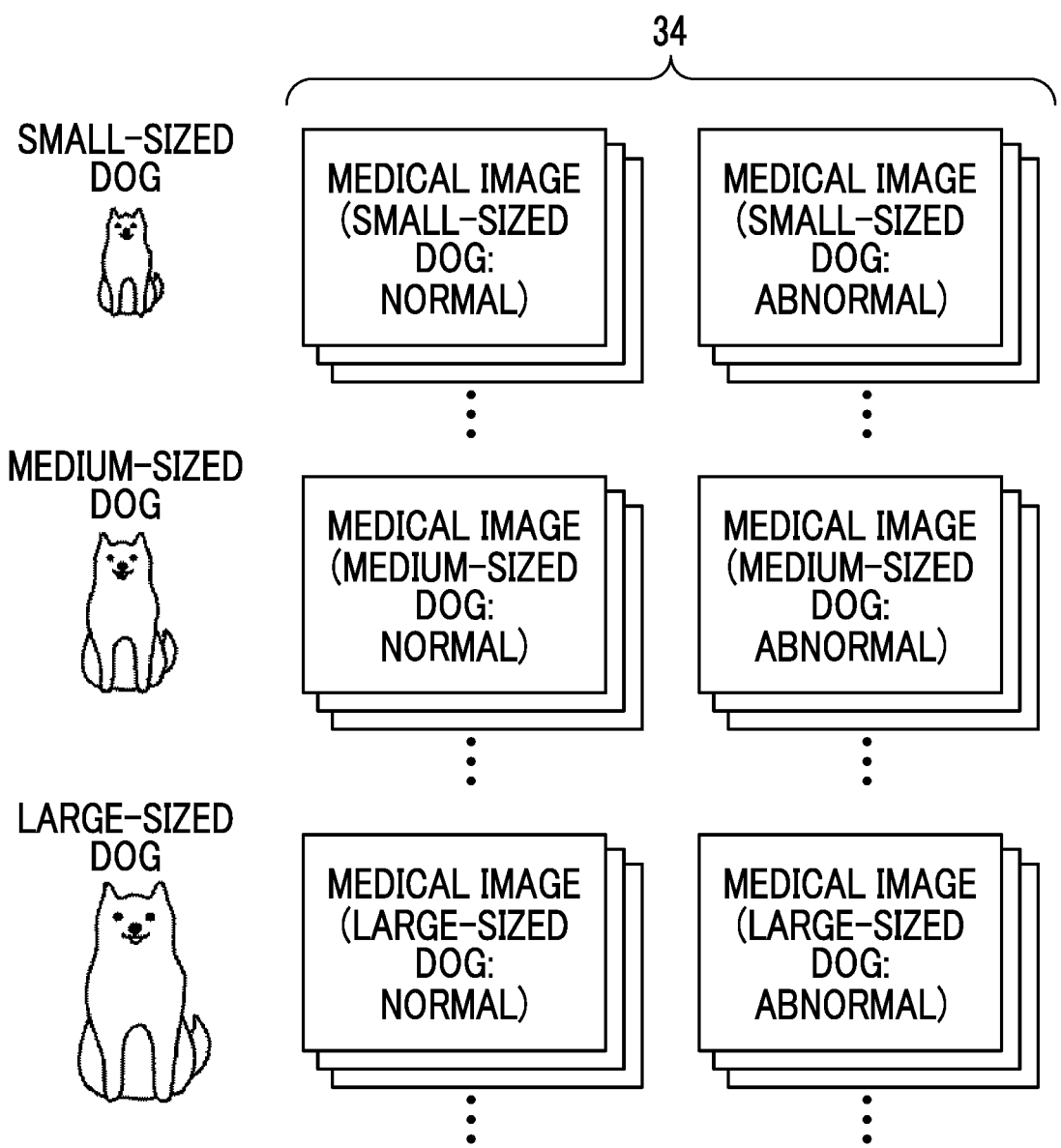
FIG. 18 is a diagram for describing information added to medical image data according to a second embodiment.

The medical image data 34 itself according to the present embodiment is the same as that of the first embodiment, but information added to the medical image data 34 is different from that in the first embodiment. As shown in FIG. 18 as an example, type information representing a type classified by weight of the dog and a type to which the dog as the subject to be imaged belongs and the abnormality presence/absence information are added to the medical image data 34.

As shown in FIG. 18, in the present embodiment, an example will be described in which the type represented by the type information is a small-sized dog, a medium-sized dog, or a large-sized dog. However, the present disclosure is not limited thereto. The type represented by the type information may be, for example, two types of small-sized dog or large-sized dog, or four or more types. In the present embodiment, a dog breed whose adult dog weighs less than 10 kg is set as the small-sized dog, a dog breed whose adult dog weighs 10 kg or more and less than 25 kg is set as the medium-sized dog, a dog breed whose adult dog weighs 25 kg or more is set as the large-sized dog, regardless of the age of the subject. The type of dog may be classified by body length or by a combination of weight and body length, not by weight.

Figure 19:
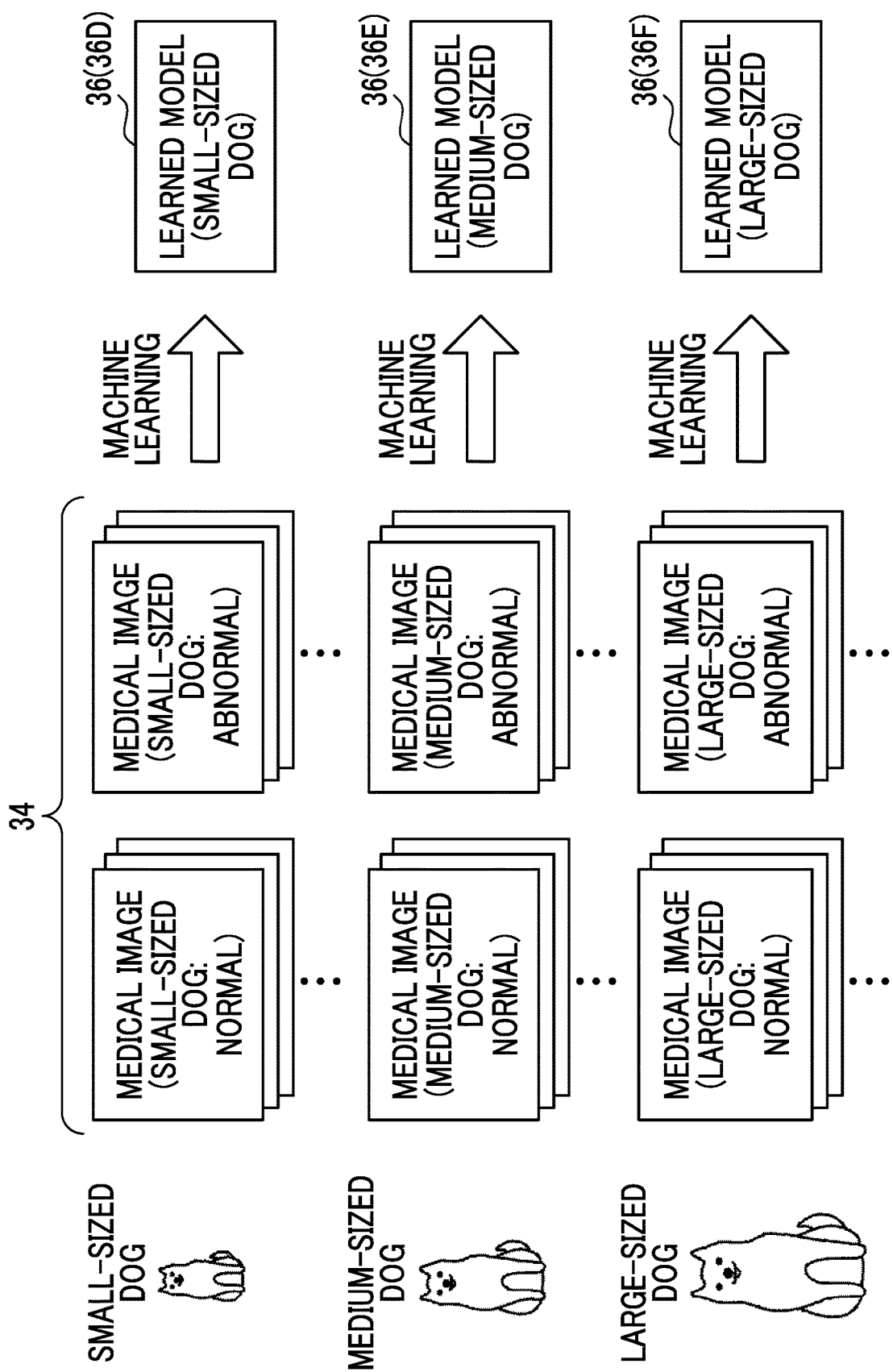
FIG. 19 is a diagram for describing a learned model for each type according to the second embodiment.

The learned model 36 according to the present embodiment is a model learned in advance using a set of the plurality of pieces of medical image data 34 for learning and the type information. In the present embodiment, as shown in FIG. 19 as an example, the learned model 36 is generated for each type by machine learning using the set of the plurality of pieces of medical image data 34 and the type information. In the following, in a case where the learned model 36 is distinguished for each type, the description will be made with an alphabet added to the end of the reference numeral, such as a learned model 36D for the small-sized dog, a learned model 36E for the medium-sized dog, and a learned model 36F for the large-sized dog. An example of the learned model 36 is a neural network model.

Figure 20:
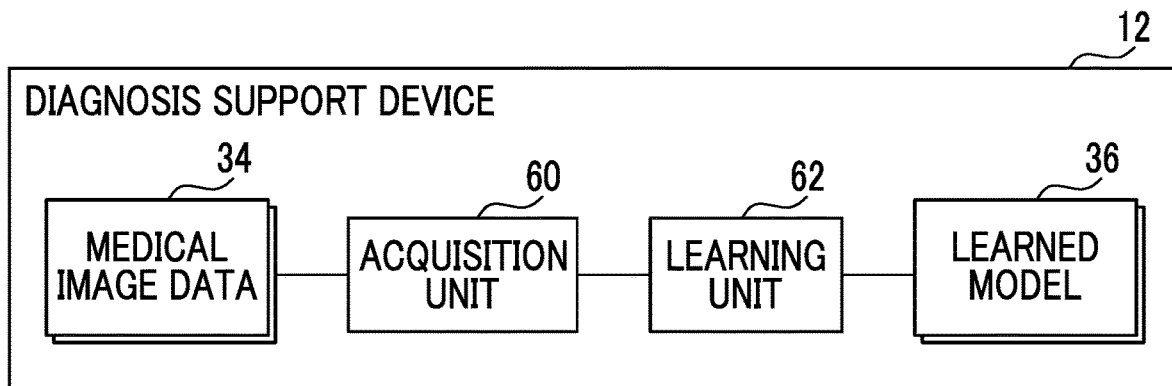
FIG. 20 is a block diagram showing an example of a functional configuration in a learning phase of a diagnosis support device according to the second embodiment.

Next, a functional configuration in a learning phase of the diagnosis support device 12 according to the present embodiment will be described with reference to FIG. 20. As shown in FIG. 20, the diagnosis support device 12 includes an acquisition unit 60 and a learning unit 62. The CPU 20 executes the learning program 30 to function as the acquisition unit 60 and the learning unit 62.

The acquisition unit 60 acquires the medical image data 34, and the type information and the abnormality presence/absence information added to the medical image data 34, from the storage unit 22.

The learning unit 62 learns a plurality of sets of the medical image data 34, the type information, and the abnormality presence/absence information acquired by the acquisition unit 60 as learning data to generate the learned model 36 that outputs information on the presence or absence of the abnormality in the medical image of the subject based on the medical image data and the type information.

More specifically, the learning unit 62 generates the learned model 36 that receives the medical image data 34 and outputs the information representing the presence or absence of the abnormality in the medical image represented by the medical image data 34, for each type represented by the type information, by machine learning.

More specifically, in a case where the medical image data 34 representing a medical image having no abnormality among the medical image data 34 of the small-sized dog is input, the learning unit 62 causes the model to learn such that information representing normality is output. In a case where the medical image data 34 representing a medical image having the abnormality among the medical image data 34 of the small-sized dog is input, the learning unit 62 causes the model to learn such that information representing abnormality is output. The learned model 36D for the small-sized dog is generated by the learning.

Similarly, in a case where the medical image data 34 representing a medical image having no abnormality among the medical image data 34 of the medium-sized dog is input, the learning unit 62 causes the model to learn such that information representing normality is output. In a case where the medical image data 34 representing a medical image having the abnormality among the medical image data 34 of the medium-sized dog is input, the learning unit 62 causes the model to learn such that information representing abnormality is output. The learned model 36E for the medium-sized dog is generated by the learning.

Similarly, in a case where the medical image data 34 representing a medical image having no abnormality among the medical image data 34 of the large-sized dog is input, the learning unit 62 causes the model to learn such that information representing normality is output. In a case where the medical image data 34 representing a medical image having the abnormality among the medical image data 34 of the large-sized dog is input, the learning unit 62 causes the model to learn such that information representing abnormality is output. The learned model 36F for the large-sized dog is generated by the learning.

Figure 21:
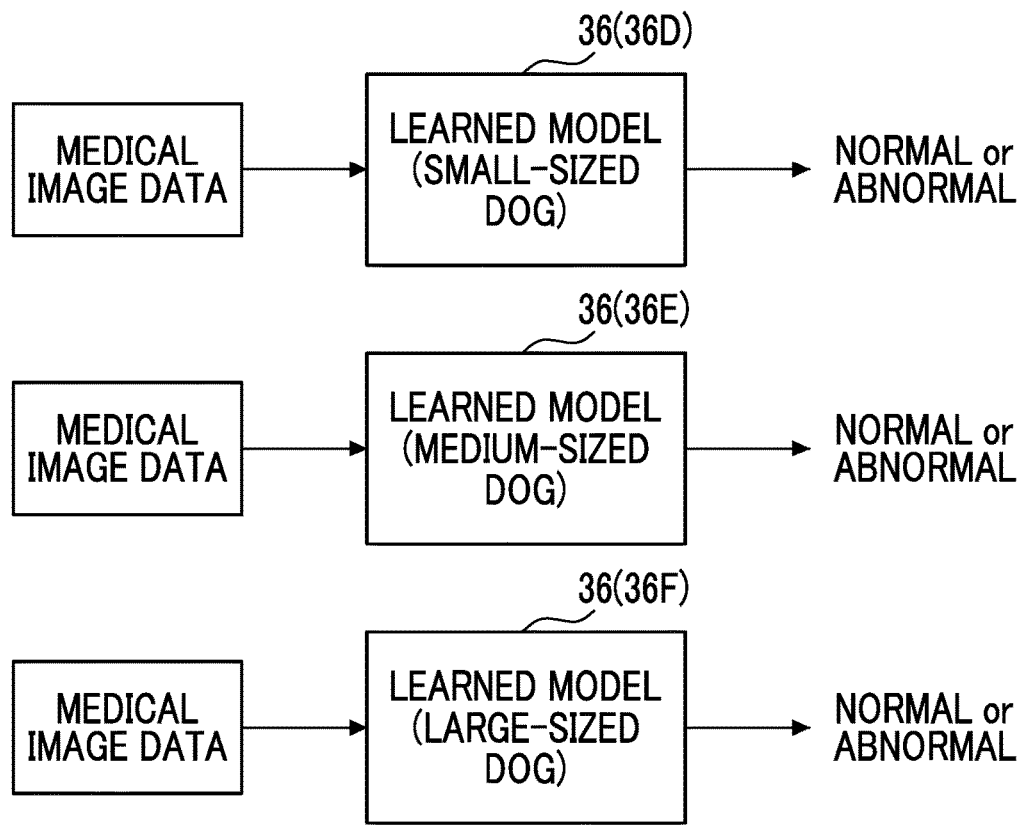
FIG. 21 is a diagram for describing inputs and outputs of the learned models according to the second embodiment.

For example, an error back propagation method can be employed as an algorithm of the learning by the learning unit 62. With the learning by the learning unit 62, as shown in FIG. 21 as an example, the learned model 36 that receives the medical image data and outputs the information representing whether the medical image represented by the received medical image data is normal or abnormal is generated for each type. The learning unit 62 stores the generated learned model 36 in the storage unit 22.

Next, an action in the learning phase of the diagnosis support device 12 according to the present embodiment will be described with reference to FIG. 22. The CPU 20 executes the learning program 30 to execute learning processing shown in FIG. 22.

Figure 22:
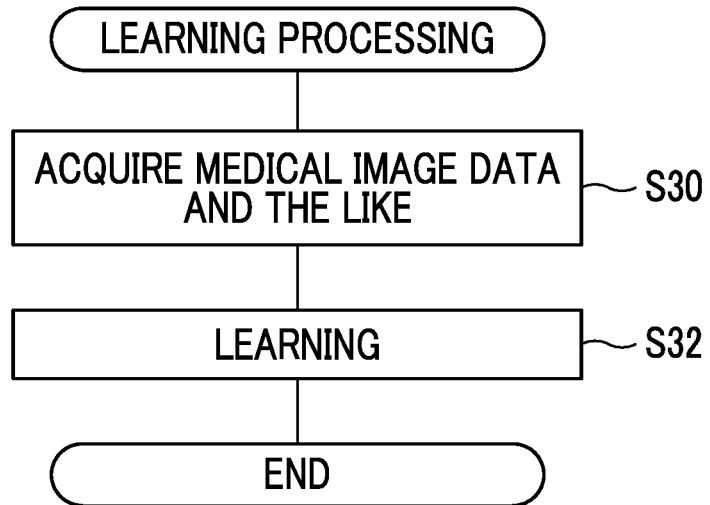
FIG. 22 is a flowchart showing an example of learning processing according to the second embodiment.

In step S30 in FIG. 22, the acquisition unit 60 acquires the medical image data 34, and the type information and the abnormality presence/absence information added to the medical image data 34, from the storage unit 22.

In step S32, as described above, the learning unit 62 causes the model to learn the plurality of sets of the medical image data 34, the type information, and the abnormality presence/absence information acquired in step S30 as learning data for each type, as described above. With the learning, the learning unit 62 generates the learned model 36 that outputs the information on the presence or absence of the abnormality in the medical image of the subject based on the medical image data and the type information. The learning unit 62 stores the generated learned model 36 in the storage unit 22. In a case where the processing of step S32 ends, the learning processing ends.

Figure 23:
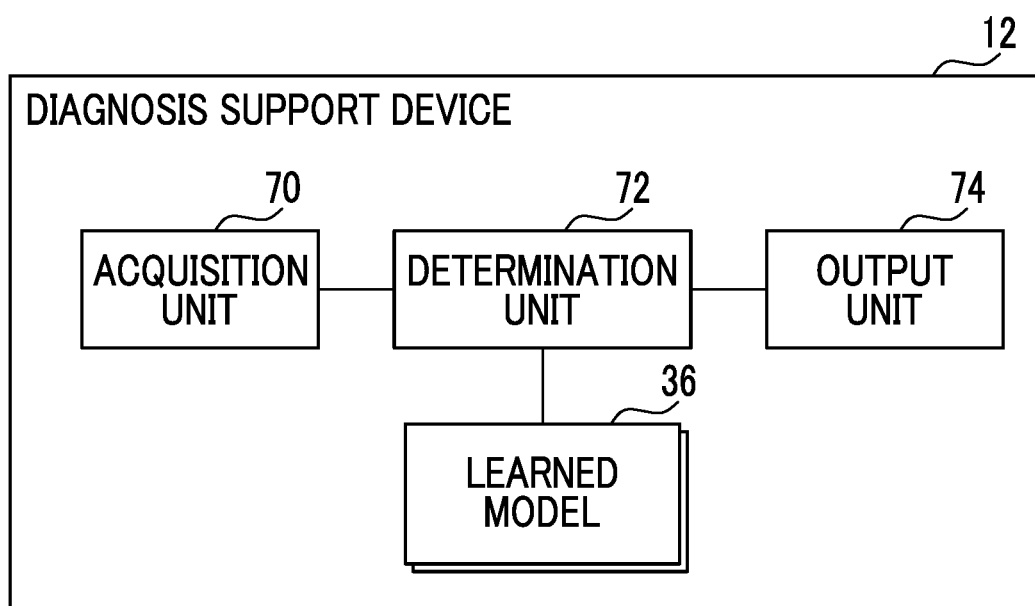
FIG. 23 is a block diagram showing an example of a functional configuration in an operation phase of the diagnosis support device according to the second embodiment.

Next, a functional configuration in an operation phase of the diagnosis support device 12 according to the present embodiment will be described with reference to FIG. 23. As shown in FIG. 23, the diagnosis support device 12 includes an acquisition unit 70, a determination unit 72, and an output unit 74. The CPU 20 executes the diagnosis support program 32 to function as the acquisition unit 70, the determination unit 72, and the output unit 74. The diagnosis support device 12 may be the same device or different devices in the learning phase and the operation phase.

The acquisition unit 70 acquires the medical image data representing the medical image obtained by imaging the animal as the subject to be diagnosed by the user such as the veterinarian with the medical image capturing device and the type information representing a type classified by weight of the animal and a type to which the subject belongs. The type information may be added to the medical image data or may be input by the user through an operation unit of the terminal device 14. In a state where a table in which a dog breed and the type are associated with each other is prepared in advance, the acquisition unit 70 may acquire a breed of the dog as the subject from an electronic medical record or the like and then type information representing a type corresponding to the acquired dog breed from the table prepared in advance.

The determination unit 72 determines the presence or absence of the abnormality in the medical image of the subject based on the medical image data and the type information acquired by the acquisition unit 70 and the learned model 36. Specifically, the determination unit 72 inputs the medical image data acquired by the acquisition unit 70 to the learned model 36 for type represented by the type information acquired by the acquisition unit 70. The learned model 36 outputs the information representing normality or the information representing abnormality in correspondence with the input medical image data.

In a case where the output from the learned model 36 is the information representing normality, the determination unit 72 determines that there is no abnormality in the medical image of the subject represented by the medical image data acquired by the acquisition unit 70. On the other hand, in a case where the output from the learned model 36 is the information representing abnormality, the determination unit 72 determines that there is the abnormality in the medical image of the subject represented by the medical image data acquired by the acquisition unit 70.

The output unit 74 outputs information representing the determination result by the determination unit 72. Specifically, the output unit 74 outputs the information representing the determination result by the determination unit 72 to the terminal device 14 to display the determination result by the determination unit 72 on a display unit of the terminal device 14. The user interprets the medical image with reference to the determination result displayed on the display unit of the terminal device 14 and diagnoses the subject.

Next, the action in the operation phase of the diagnosis support device 12 according to the present embodiment will be described with reference to FIG. 24. The CPU 20 executes the diagnosis support program 32 to execute diagnosis support processing shown in FIG. 24.

Figure 24:
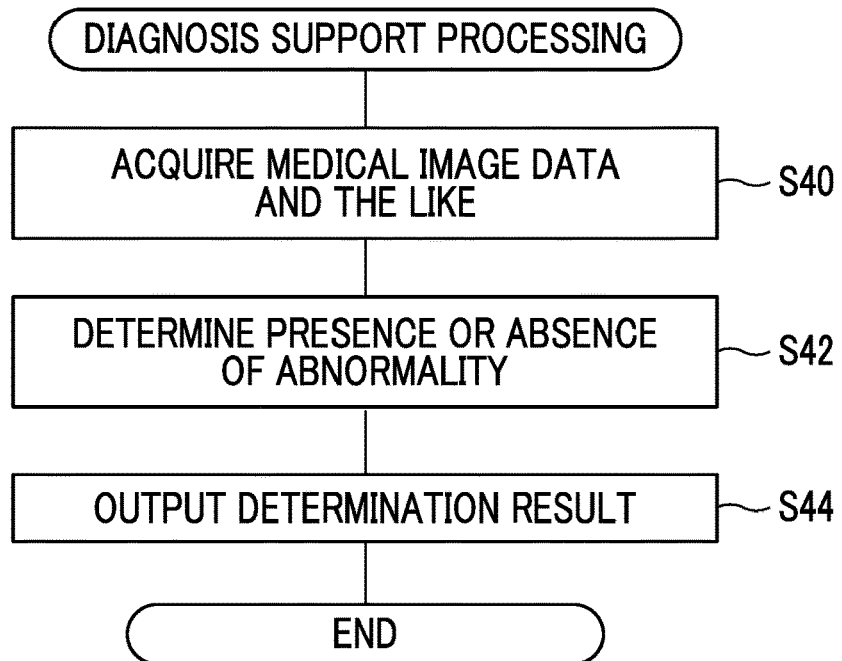
FIG. 24 is a flowchart showing an example of diagnosis support processing according to the second embodiment.

In step S40 of FIG. 24, the acquisition unit 70 acquires the medical image data representing the medical image obtained by imaging the animal as the subject to be diagnosed by the user with the medical image capturing device and the type information representing the type of the subject.

In step S42, the determination unit 72 determines the presence or absence of the abnormality in the medical image of the subject based on the medical image data and the type information acquired in step S40 and the learned model 36, as described above. In step S44, the output unit 74 outputs the information representing the determination result of the processing of step S42 as described above. In a case where the processing of step S44 ends, the diagnosis support processing ends.

Figure 25:
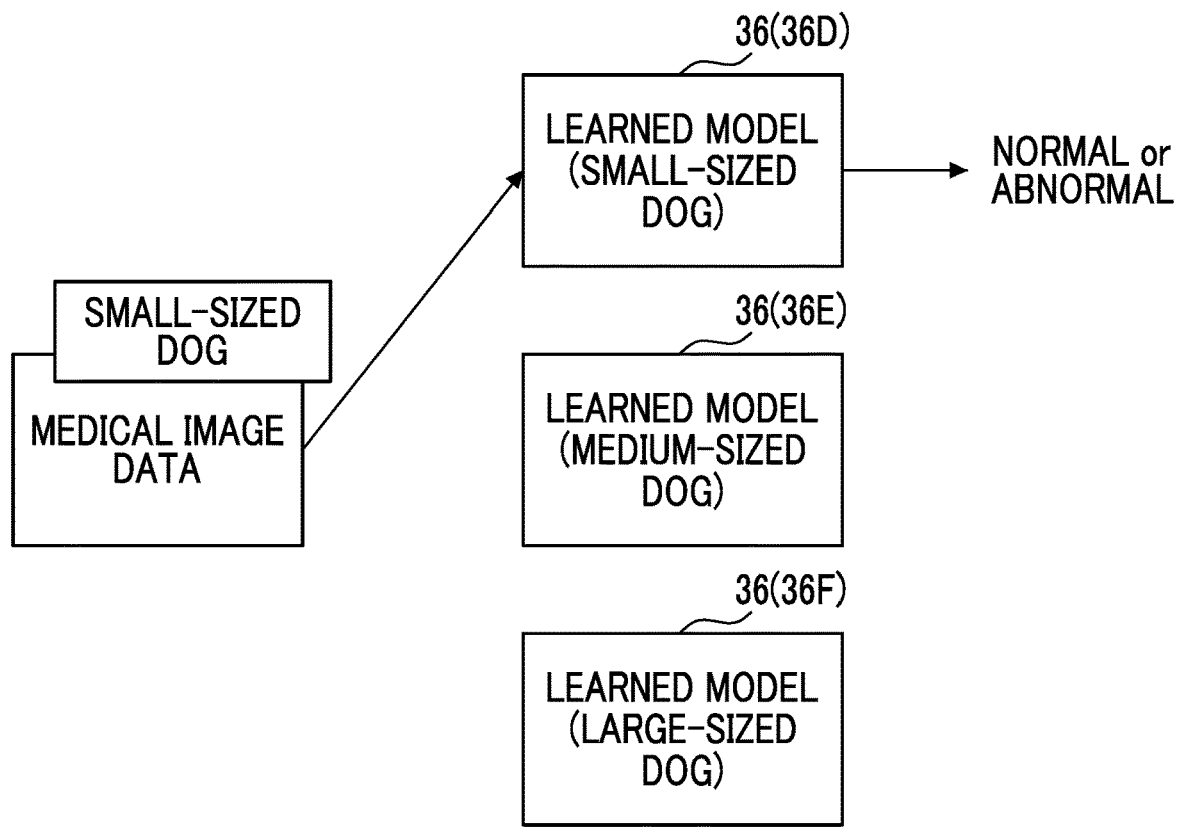
FIG. 25 is a diagram showing determination processing using a learned model for a small-sized dog.
Figure 26:
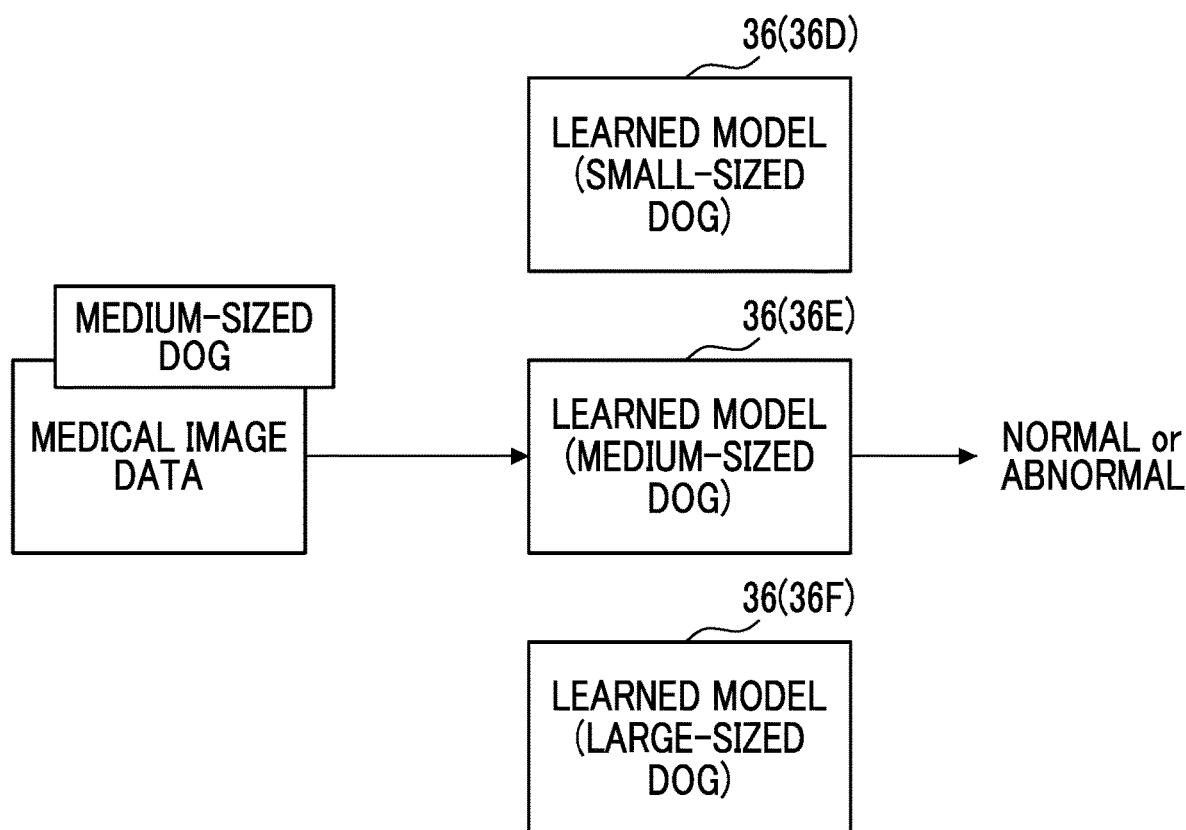
FIG. 26 is a diagram showing determination processing using a learned model for a medium-sized dog.
Figure 27:
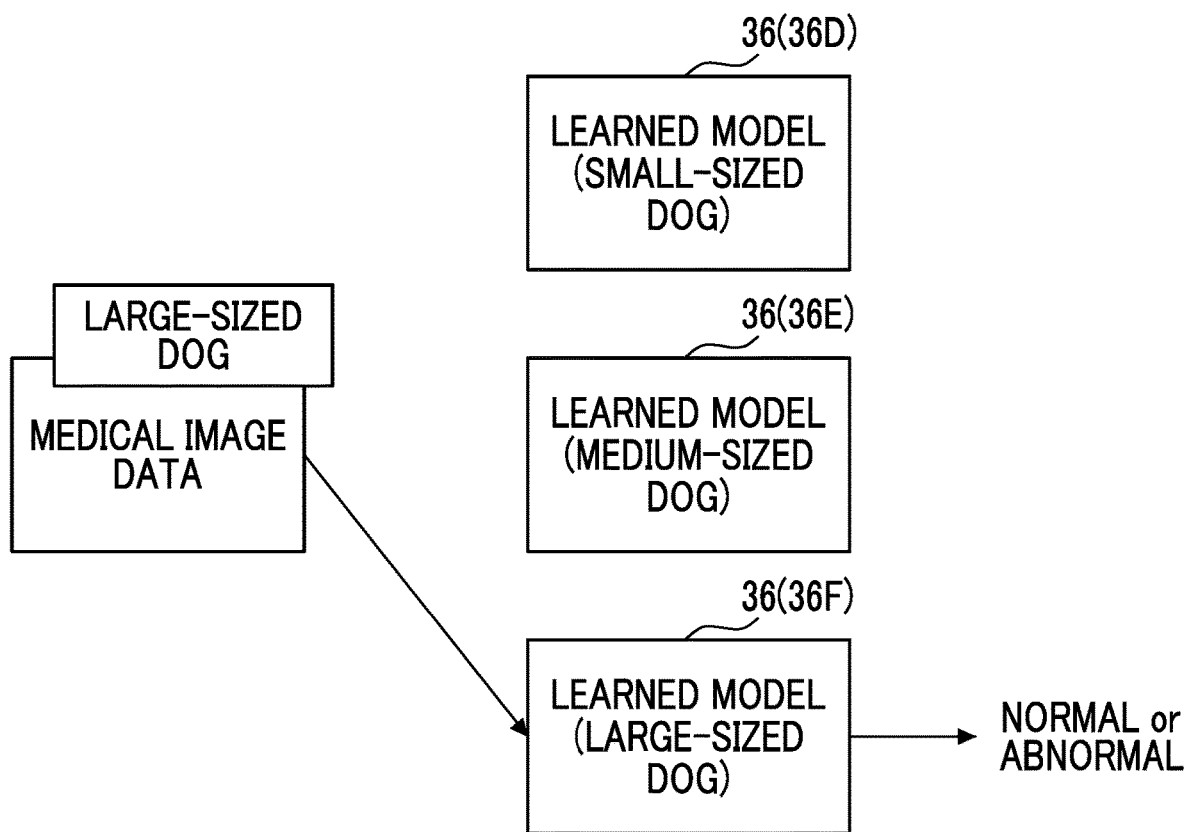
FIG. 27 is a diagram showing determination processing using a learned model for a large-sized dog.

As described above, according to the present embodiment, the presence or absence of the abnormality in the medical image of the subject is determined based on the medical image data, the type information, and the learned model 36. Specifically, as shown in FIG. 25, in a case where the subject is the small-sized dog, the medical image data is input to the learned model 36D for the small-sized dog and the presence or absence of the abnormality in the medical image is determined. As shown in FIG. 26, in a case where the subject is the medium-sized dog, the medical image data is input to the learned model 36E for the medium-sized dog and the presence or absence of the abnormality in the medical image is determined. As shown in FIG. 27, in a case where the subject is the large-sized dog, the medical image data is input to the learned model 36F for the large-sized dog and the presence or absence of the abnormality in the medical image is determined.

Therefore, it is possible to accurately determine the presence or absence of an abnormality in the medical image in consideration of a difference in feature of the medical image depending on the types classified by the weight. As a result, it is possible to effectively support the diagnosis using the medical image.

Figure 28:
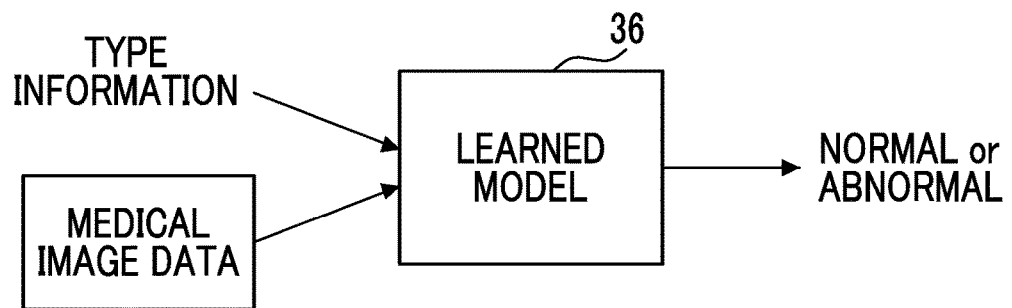
FIG. 28 is a diagram showing an example of a learned model in a case where the medical image data and type information are input.

In the second embodiment, the case is described in which the learned model 36 that receives the medical image data is generated for each type. However, the present disclosure is not limited thereto. For example, one learned model 36 that receives the medical image data and the type information may be generated as shown in FIG. 28.

Figure 29:
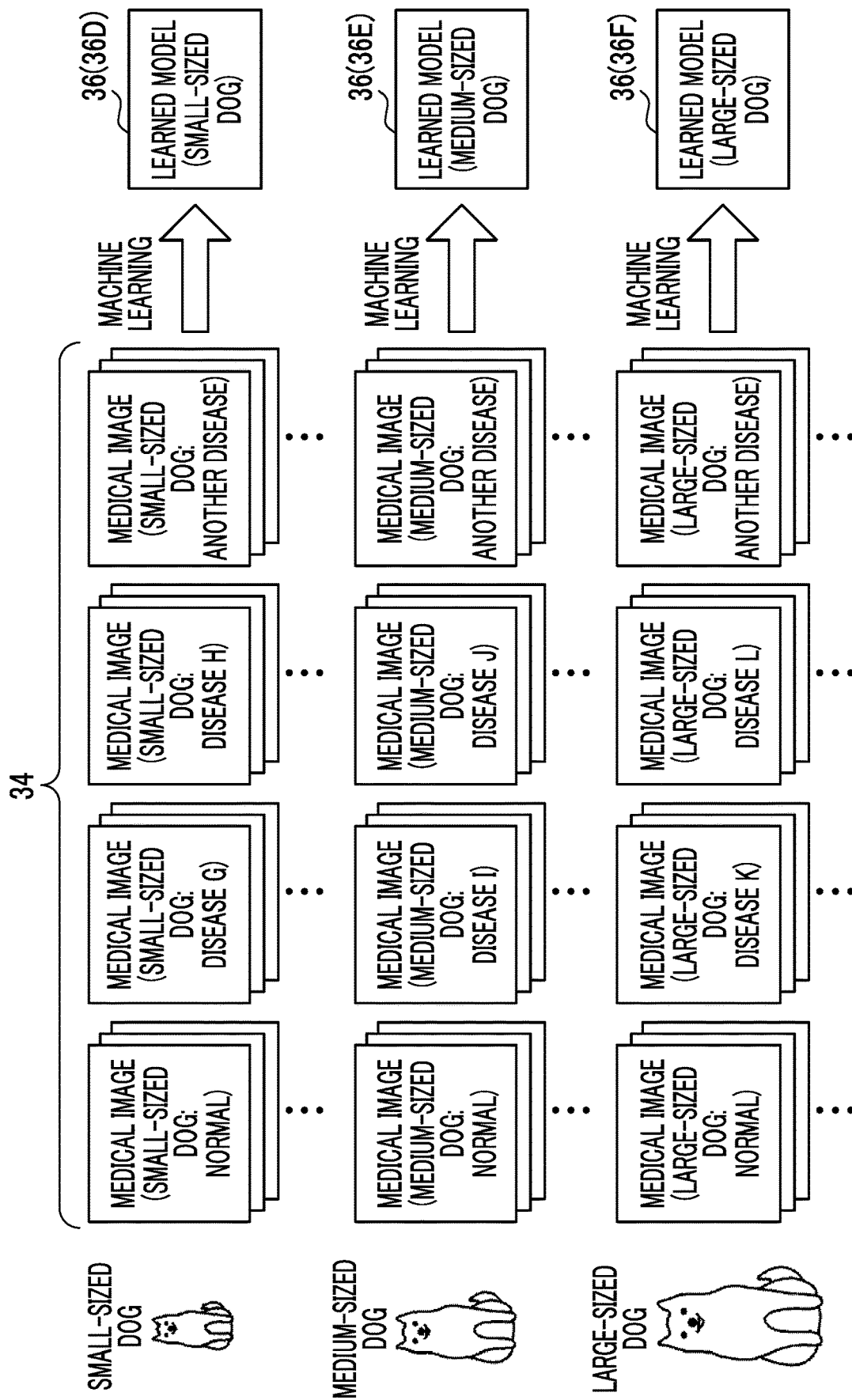
FIG. 29 is a diagram for describing a learned model for each type according to a modification example.

In the second embodiment, the case is described in which the second medical image including the lesion corresponding to the disease is used as one type of medical image without being classified. However, the present disclosure is not limited thereto. For example, as shown in FIG. 29, the second medical image may be classified for each disease determined in advance as a disease that is likely to be suffered for each type. FIG. 29 shows an example in which the second medical image of the small-sized dog is classified into three types of "disease G", "disease H", and "another disease (that is, disease other than disease G and disease H)". In the example of FIG. 29, the "disease G" and "disease H" are diseases determined in advance as diseases that the small-sized dog is likely to suffer. Examples of the disease that the small-sized dog is likely to suffer include patellar dislocation, radioulnar fracture, and Legg-Calve-Perthes disease.

FIG. 29 shows an example in which the second medical image of the medium-sized dog is classified into three types of "disease I", "disease J", and "another disease (that is, disease other than disease I and disease J)". In the example of FIG. 29, the "disease I" and the "disease J" are diseases determined in advance as diseases that the medium-sized dog is likely to suffer. Examples of the disease that the medium-sized dog is likely to suffer include patellar dislocation and hip joint disease.

FIG. 29 shows an example in which the second medical image of the large-sized dog is classified into three types of "disease K", "disease L", and "another disease (that is, disease other than disease K and disease L)". In the example of FIG. 29, the "disease K" and the "disease L" are diseases determined in advance as diseases that the large-sized dog is likely to suffer. Examples of the disease that the large-sized dog is likely to suffer include hip joint disease, cauda equina syndrome, and anterior cruciate ligament rupture.

In this example, as shown in FIG. 30 as an example, a probability that the medical image represented by the input medical image data is normal, a probability that the medical image corresponds to disease G, a probability that the medical image corresponds to disease H, and a probability that the medical image corresponds to another disease are output from the learned model 36D for the small-sized dog. In this example, a probability that the medical image represented by the input medical image data is normal, a probability that the medical image corresponds to disease I, a probability that the medical image corresponds to disease J, and a probability that the medical image corresponds to another disease are output from the learned model 36E for the medium-sized dog. In this example, a probability that the medical image represented by the input medical image data is normal, a probability that the medical image corresponds to disease K, a probability that the medical image corresponds to disease L, and a probability that the medical image corresponds to another disease are output from the learned model 36F for the large-sized dog.

In this embodiment, for example, in a case where the probability that the medical image is normal among the outputs from the learned model 36 is the highest, the determination unit 72 determines that there is no abnormality in the medical image of the subject represented by the medical image data acquired by the acquisition unit 70. In this embodiment, for example, in a case where any probability other than the probability that the medical image is normal among the outputs from the learned model 36 is the highest, the determination unit 72 determines that there is the abnormality in the medical image of the subject represented by the medical image data acquired by the acquisition unit 70. In a case where a total value of the probabilities corresponding to respective diseases other than the probability that the medical image is normal among the outputs from the learned model 36 is higher than the probability that the medical image is normal, the determination unit 72 may determine that there is the abnormality in the medical image of the subject represented by the medical image data acquired by the acquisition unit 70. In this case, in a case where the total value of the probabilities corresponding to respective diseases other than the probability that the medical image is normal among the outputs from the learned model 36 is equal to or less than the probability that the medical image is normal, the determination unit 72 may determine that there is no abnormality in the medical image of the subject represented by the medical image data acquired by the acquisition unit 70. In this example, the medical image data for learning is classified for each easily collected disease. Therefore, it is possible to determine the presence or absence of the disease more accurately.

In this example, in a case where the determination unit 72 determines that there is the abnormality in the medical image of the subject, the output unit 74 may output a disease name to which the medical image corresponds with the highest probability or may output disease names in descending order of the corresponding probability.

In the second embodiment, the determination unit 72 may determine the type of the subject from the weight of the subject. In this case, in a case where the weight of the subject is less than a first threshold value TH1 (for example, 10 kg), the determination unit 72 determines that the type of the subject is the small-sized dog. In this case, in a case where the weight of the subject is the first threshold value TH1 or more and less than a second threshold value TH2 (for example, 25 kg), the determination unit 72 determines that the type of the subject is the medium-sized dog. In this case, in a case where the weight of the subject is equal to or larger than the second threshold value TH2 (for example, 25 kg), the determination unit 72 determines that the type of the subject is the large-sized dog. In this case, the acquisition unit 70 acquires type information representing the type of the subject determined by the determination unit 72.

The first embodiment and the second embodiment may be combined. In this case, for example, a form is exemplified in which the learned model 36 is generated for each combination of the head species represented by the head species information and the type represented by the type information.

In each of the above embodiments, the case where the dog is employed as the subject animal is described. However, the present disclosure is not limited thereto. For example, an animal other than the dog such as a cat may be employed as the subject animal.

The following various processors may be used as a hardware structure of a processing unit that executes various pieces of processing such as each functional unit of the diagnosis support device 12 in each of the above embodiments. The various processors include a programmable logic device (PLD) which is a processor whose circuit configuration is changeable after manufacturing such as an FPGA, a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units as described above.

One processing unit may be configured by one of the various processors or a combination of two or more processors of the same type or different types (for example, a combination of a plurality of FPGAs or a combination of a CPU and an FPGA). A plurality of processing units may be configured by one processor. As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

Further, more specifically, a circuitry combining circuit elements such as semiconductor elements can be used as the hardware structure of the various processors.

Further, in the above embodiments, the mode is described in which the learning program 30 and the diagnosis support program 32 are stored (installed) in the storage unit 22 in advance. However, the present disclosure is not limited thereto. The learning program 30 and the diagnosis support program 32 may be provided in a mode recorded on a recording medium such as a compact disc read-only memory (CD-ROM), a digital versatile disc read-only memory (DVD-ROM), and a Universal Serial Bus (USB) memory. The learning program 30 and the diagnosis support program 32 may be downloaded from an external device through a network.

Regarding the above embodiments, the following additional item is further disclosed.

Additional Item 1

A diagnosis support device comprising:
an acquisition unit that acquires medical image data representing a medical image obtained by imaging an animal as a subject with a medical image capturing device and head species information representing a head species of the subject; and
a learning unit that learns a plurality of sets of the medical image data and the head species information acquired by the acquisition unit as learning data to generate a learned model that outputs information on presence or absence of an abnormality in the medical image of the subject based on the medical image data and the head species information

What is claimed is:

1. A diagnosis support device comprising:
a memory; and
a processor coupled to the memory and configured to:
acquire medical image data representing a medical image obtained by imaging an animal as a subject with a medical image capturing device and head species information representing a head species of the subject; and
determine presence or absence of an abnormality in the medical image of the subject based on the acquired medical image data and the acquired head species information and a learned model learned in advance using a set of a plurality of pieces of the medical image data for learning, wherein the plurality of pieces of medical image data for learning are image data of subjects belonging to the acquired head species information.

2. The diagnosis support device according to claim 1, wherein the plurality of pieces of the medical image data for learning include first medical image data representing a first medical image not including a lesion and second medical image data representing a second medical image including a lesion corresponding to a disease.

3. The diagnosis support device according to claim 2, wherein the second medical image includes a medical image classified for each disease determined in advance as a disease that is likely to be suffered for each head species.

4. The diagnosis support device according to claim 1, wherein the processor is further configured to:
   determine the head species of the subject, using an optical image obtained by imaging a head portion of the subject, and
   acquire the head species information representing the head species of the subject that is determined.

5. The diagnosis support device according to claim 1, wherein the subject is a dog, and
   wherein the head species is a short-headed species, a middle-headed species, or a long-headed species.

6. The diagnosis support device according to claim 1, wherein the processor is further configured to:
   obtain, in advance, a plurality of learned models for a plurality of head species of the subject, and
   select, from the plurality of learned models, a learned model for the head species corresponding to the acquired head species information to be used for determining presence or absence of an abnormality in the medical image of the subject.

7. A diagnosis support method executed by a computer, the method comprising:
   acquiring medical image data representing a medical image obtained by imaging an animal as a subject with a medical image capturing device and head species information representing a head species of the subject; and
   determining presence or absence of an abnormality in the medical image of the subject based on the acquired medical image data and acquired head species information and a learned model learned in advance using a set of a plurality of pieces of the medical image data for learning, wherein the plurality of pieces of the medical image data for learning are image data of subjects belonging to the acquired head species information.

8. The diagnosis support method according to claim 7, further comprising:
   obtaining, in advance, a plurality of learned models for a plurality of head species of the subject, and
   selecting, from the plurality of learned models, a learned model for the head species corresponding to the acquired head species information to be used for determining presence or absence of an abnormality in the medical image of the subject.

9. A non-transitory computer-readable storage medium storing a diagnosis support program for causing a computer to execute processing, the processing comprising:
   acquiring medical image data representing a medical image obtained by imaging an animal as a subject with a medical image capturing device and head species information representing a head species of the subject; and
   determining presence or absence of an abnormality in the medical image of the subject based on the acquired medical image data and acquired head species information and a learned model learned in advance using a set of a plurality of pieces of the medical image data for learning wherein the plurality of pieces of the medical image data for learning are image data of subjects belong to the acquired head species information.

10. The non-transitory computer-readable storage medium according to claim 9, wherein the processing further comprises:
    obtaining, in advance, a plurality of learned models for a plurality of head species of the subject, and
    selecting, from the plurality of learned models, a learned model for the head species corresponding to the acquired head species information to be used for determining presence or absence of an abnormality in the medical image of the subject.

\* \* \* \* \*